(12) United States Patent
Souter et al.

(10) Patent No.: US 11,473,039 B2
(45) Date of Patent: *Oct. 18, 2022

(54) WATER-SOLUBLE UNIT DOSE ARTICLES MADE FROM A COMBINATION OF DIFFERENT FILMS

(71) Applicant: MONOSOL, LLC, Merrillville, IN (US)

(72) Inventors: Philip Frank Souter, Northumberland (GB); Robby Renilde Francois Keuleers, Lippelo (BE); Regine Labeque, Brussels (BE); Florence Catherine Courchay, Wemmel (BE); Marc Rene Bert Renmans, Strombeek-Bever (BE); David M. Lee, Crown Point, IN (US); Steven G. Friedrich, Crown Point, IN (US); Lee K. Yeung, Highland, IN (US); Shinsuke Nii, Merrillville, IN (US)

(73) Assignee: MONOSOL, LLC, Merrillville, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/601,224

(22) Filed: Oct. 14, 2019

(65) Prior Publication Data

US 2020/0040288 A1 Feb. 6, 2020

Related U.S. Application Data

(63) Continuation of application No. 15/620,316, filed on Jun. 12, 2017, now Pat. No. 10,443,024.

(Continued)

(51) Int. Cl.
*C11D 17/00* (2006.01)
*C11D 17/04* (2006.01)
(Continued)

(52) U.S. Cl.
CPC ............ *C11D 17/042* (2013.01); *B29C 51/02* (2013.01); *B29C 66/7352* (2013.01);
(Continued)

(58) Field of Classification Search
CPC .................................................... C11D 17/042
See application file for complete search history.

(56) References Cited

U.S. PATENT DOCUMENTS 1,029,446 A 6/1912 Hunt
1,079,965 A 12/1913 Walters
(Continued)

FOREIGN PATENT DOCUMENTS

CA 2913731 A1 12/2014
CN 105377965 A 3/2016
(Continued)

OTHER PUBLICATIONS

Gordon et al., The Chemist's Companion, pp. 30-36, John Wiley & Sons Publishing (1972).
(Continued)

*Primary Examiner* — Necholus Ogden, Jr.
(74) *Attorney, Agent, or Firm* — Marshall, Gerstein & Borun LLP

(57) ABSTRACT

The present disclosure relates to pouches made from a combination of chemically different water-soluble films and optionally containing a composition (e.g. a household care composition or non-household care composition) that is at least partially enclosed by the water-soluble films in at least one compartment.

57 Claims, 4 Drawing Sheets

Related U.S. Application Data

(60) Provisional application No. 62/349,655, filed on Jun. 13, 2016.

(51) Int. Cl.

| | | |
|---|---|---|
| *B29C 51/02* | (2006.01) | |
| *B29C 65/00* | (2006.01) | |
| *B65D 53/06* | (2006.01) | |
| *B65D 65/46* | (2006.01) | |
| *C07C 31/20* | (2006.01) | |
| *C07C 57/145* | (2006.01) | |
| *C08J 5/12* | (2006.01) | |
| *C08K 5/00* | (2006.01) | |
| *C08K 5/053* | (2006.01) | |
| *C08L 29/04* | (2006.01) | |
| *B29K 29/00* | (2006.01) | |

(52) U.S. Cl.
CPC ............ *B65D 53/06* (2013.01); *B65D 65/46* (2013.01); *C07C 31/202* (2013.01); *C07C 57/145* (2013.01); *C08J 5/121* (2013.01); *C08K 5/0016* (2013.01); *C08K 5/053* (2013.01); *C08L 29/04* (2013.01); *B29K 2029/04* (2013.01); *C11D 17/043* (2013.01); *C11D 17/045* (2013.01)

(56) References Cited

U.S. PATENT DOCUMENTS

| | | | |
|---|---|---|---|
| 3,580,390 A | 5/1971 | Shull, Jr. | |
| 3,892,905 A | 7/1975 | Albert | |
| RE29,059 E | 12/1976 | Kack et al. | |
| 4,119,604 A | 10/1978 | Wysong | |
| 4,155,971 A | 5/1979 | Wysong | |
| 4,156,047 A | 5/1979 | Wysong | |
| 4,466,431 A | 8/1984 | Tharrat et al. | |
| 4,626,372 A | 12/1986 | Kaufmann et al. | |
| 4,681,228 A | 7/1987 | Kerry et al. | |
| 4,692,494 A | 9/1987 | Sonenstein | |
| 4,747,976 A | 5/1988 | Yang et al. | |
| 4,885,105 A | 12/1989 | Yang et al. | |
| 5,135,982 A | 8/1992 | Matsumoto et al. | |
| 5,316,688 A | 5/1994 | Gladfelter et al. | |
| 5,362,532 A | 11/1994 | Famili et al. | |
| 5,558,228 A | 9/1996 | Jackisch et al. | |
| 5,674,578 A | 10/1997 | Giori | |
| 5,691,015 A | 11/1997 | Tsukamoto et al. | |
| 6,204,223 B1 | 3/2001 | Holmes et al. | |
| 6,787,512 B1 | 9/2004 | Verrall et al. | |
| 6,960,627 B2 | 11/2005 | Huth et al. | |
| 7,022,656 B2 | 4/2006 | Verrall et al. | |
| 7,067,575 B2 | 6/2006 | Kitamura et al. | |
| 7,476,325 B2 | 1/2009 | Tufano et al. | |
| 7,547,737 B2 | 6/2009 | Kochvar et al. | |
| 7,642,226 B2 | 1/2010 | Verrall et al. | |
| 7,749,952 B2 | 7/2010 | Zhang et al. | |
| 7,754,318 B2 | 7/2010 | Kitamura et al. | |
| 7,786,027 B2 | 8/2010 | Aouad et al. | |
| 7,867,968 B1 | 1/2011 | Aouad | |
| 7,871,976 B1 | 1/2011 | Aouad | |
| 8,163,104 B2 | 4/2012 | Swidersky et al. | |
| 8,276,756 B2 | 10/2012 | Denome et al. | |
| 8,333,033 B2 | 12/2012 | Bell | |
| 8,697,624 B2 | 4/2014 | Denome et al. | |
| 8,728,593 B2 | 5/2014 | Vicari et al. | |
| 8,754,025 B2 | 6/2014 | Wiedemann et al. | |
| 8,835,372 B2 | 9/2014 | Jennewein | |
| 8,905,236 B2 | 12/2014 | Denome et al. | |
| 8,980,817 B2 | 3/2015 | Wiedemann et al. | |
| 9,133,329 B2 | 9/2015 | Denome et al. | |
| 9,267,098 B2 | 2/2016 | Miracle | |
| 9,404,071 B2 | 8/2016 | Labeque et al. | |
| 10,183,794 B2 | 1/2019 | Souter et al. | |
| 10,240,114 B2 | 3/2019 | Labeque et al. | |
| 10,336,973 B2 | 7/2019 | Labeque et al. | |
| 10,370,627 B2 | 8/2019 | Courchay et al. | |
| 10,377,980 B2 | 8/2019 | Souter et al. | |
| 10,619,042 B2 | 4/2020 | Labeque et al. | |
| 10,745,655 B2 | 8/2020 | Courchay et al. | |
| 2004/0072709 A1 | 4/2004 | Wiedemann et al. | |
| 2004/0092635 A1* | 5/2004 | Kitamura .................. C08J 5/18 524/386 | |
| 2004/0144682 A1 | 7/2004 | Altmayer | |
| 2006/0172910 A1 | 8/2006 | Brooker et al. | |
| 2006/0173430 A1 | 8/2006 | Lee et al. | |
| 2007/0003719 A1 | 1/2007 | Balchin | |
| 2008/0081774 A1 | 4/2008 | Koch | |
| 2008/0097029 A1 | 4/2008 | Yang | |
| 2008/0110370 A1 | 5/2008 | Verrall et al. | |
| 2008/0146481 A1 | 6/2008 | Brown et al. | |
| 2008/0185347 A1 | 8/2008 | Tufano et al. | |
| 2009/0134054 A1* | 5/2009 | Lee ........... B65D 65/46 206/531 | |
| 2009/0215664 A1 | 8/2009 | Raehse | |
| 2009/0291282 A1 | 11/2009 | Kitamura et al. | |
| 2009/0312220 A1 | 12/2009 | Boutoille et al. | |
| 2010/0113318 A1 | 5/2010 | Wiedemann et al. | |
| 2010/0180549 A1 | 7/2010 | Ayats et al. | |
| 2011/0054111 A1 | 3/2011 | McLachlan et al. | |
| 2011/0062308 A1 | 3/2011 | Hammond et al. | |
| 2011/0152163 A1 | 6/2011 | Labeque et al. | |
| 2011/0186467 A1 | 8/2011 | Denome et al. | |
| 2011/0188784 A1 | 8/2011 | Denome et al. | |
| 2011/0189413 A1 | 8/2011 | Denome et al. | |
| 2012/0164424 A1* | 6/2012 | Vicari ............. C08F 218/08 428/220 | |
| 2012/0294969 A1 | 11/2012 | Koch et al. | |
| 2013/0181382 A1* | 7/2013 | Aich .............. B65D 65/46 264/571 | |
| 2013/0240388 A1 | 9/2013 | Koch et al. | |
| 2014/0110301 A1 | 4/2014 | Carrier et al. | |
| 2014/0124454 A1 | 5/2014 | Nichols et al. | |
| 2014/0162929 A1 | 6/2014 | Labeque et al. | |
| 2014/0345064 A1 | 11/2014 | Koch et al. | |
| 2014/0356603 A1 | 12/2014 | Kumar et al. | |
| 2014/0371411 A1 | 12/2014 | DiPietro et al. | |
| 2015/0074919 A1 | 3/2015 | Miracle | |
| 2015/0080561 A1 | 3/2015 | Torres et al. | |
| 2015/0093526 A1 | 4/2015 | Denome et al. | |
| 2015/0158646 A1 | 6/2015 | Meier et al. | |
| 2015/0184116 A1 | 7/2015 | Wiedemann et al. | |
| 2015/0210969 A1 | 7/2015 | Brandt-Sanz et al. | |
| 2015/0275152 A1 | 10/2015 | Brooker et al. | |
| 2015/0336692 A1 | 11/2015 | Brandt Sanz et al. | |
| 2016/0024446 A1 | 1/2016 | Lee et al. | |
| 2016/0102278 A1 | 4/2016 | Labeque et al. | |
| 2016/0102279 A1 | 4/2016 | Labeque et al. | |
| 2016/0172910 A1 | 6/2016 | Saito et al. | |
| 2016/0200501 A1 | 7/2016 | Lee et al. | |
| 2016/0251144 A1* | 9/2016 | Elgamal ............. B65D 5/5035 206/457 | |
| 2016/0251148 A1 | 9/2016 | Edwards | |
| 2016/0326285 A1 | 11/2016 | Mori et al. | |
| 2017/0218146 A1 | 8/2017 | Childers et al. | |
| 2017/0226298 A1 | 8/2017 | Friedrich et al. | |
| 2017/0226338 A1 | 8/2017 | Friedrich et al. | |
| 2017/0233539 A1 | 8/2017 | Friedrich et al. | |
| 2017/0259976 A1 | 9/2017 | Lee et al. | |
| 2017/0275394 A1 | 9/2017 | Mori et al. | |
| 2017/0298216 A1 | 10/2017 | Labeque et al. | |
| 2017/0298308 A1 | 10/2017 | Labeque et al. | |
| 2017/0355934 A1 | 12/2017 | Courchay et al. | |
| 2017/0355935 A1 | 12/2017 | Courchay et al. | |
| 2017/0355936 A1 | 12/2017 | Souter et al. | |
| 2017/0355937 A1 | 12/2017 | Courchay et al. | |
| 2017/0355938 A1 | 12/2017 | Lee et al. | |
| 2017/0369217 A1 | 12/2017 | Souter et al. | |
| 2017/0369822 A1 | 12/2017 | Souter et al. | |
| 2017/0369823 A1 | 12/2017 | Souter et al. | |
| 2018/0002647 A1 | 1/2018 | Souter et al. | |
| 2018/0127200 A1 | 5/2018 | Edwards | |
| 2019/0276782 A1 | 9/2019 | Labeque et al. | |

(56) References Cited

U.S. PATENT DOCUMENTS

| | | |
|---|---|---|
| 2020/0048587 A1 | 2/2020 | Courchay et al. |
| 2020/0199344 A1 | 6/2020 | Labeque et al. |
| 2020/0339920 A1 | 10/2020 | Courchay et al. |

FOREIGN PATENT DOCUMENTS

| | | |
|---|---|---|
| CN | 105601974 A | 5/2016 |
| EP | 0291198 A2 | 11/1988 |
| EP | 0407301 A1 | 1/1991 |
| EP | 0989803 A1 | 4/2000 |
| EP | 01298196 A1 | 4/2003 |
| EP | 1432614 A1 | 6/2004 |
| EP | 1466938 A1 | 10/2004 |
| EP | 1512701 | 3/2005 |
| EP | 2021172 B1 | 5/2010 |
| EP | 2258820 A1 | 12/2010 |
| EP | 2049587 B1 | 3/2013 |
| EP | 3025848 A1 | 6/2016 |
| EP | 3138896 A1 | 3/2017 |
| EP | 3202880 A1 | 8/2017 |
| EP | 3207083 A1 | 8/2017 |
| EP | 3207085 A2 | 8/2017 |
| JP | S52015576 A | 2/1977 |
| JP | S55-125865 A | 9/1980 |
| JP | H0370760 B2 | 11/1991 |
| JP | H04164998 A | 6/1992 |
| JP | H5239152 A | 9/1993 |
| JP | H06298273 A | 10/1994 |
| JP | H06298274 A | 10/1994 |
| JP | H06340899 A | 12/1994 |
| JP | H08229112 A | 9/1996 |
| JP | H08244835 A | 9/1996 |
| JP | H09040834 A | 2/1997 |
| JP | H09272773 A | 10/1997 |
| JP | H09324096 A | 12/1997 |
| JP | 2000169896 A | 6/2000 |
| JP | 2001247625 A | 9/2001 |
| JP | 2002003896 A | 1/2002 |
| JP | 2002003897 A | 1/2002 |
| JP | 2003-011590 A | 1/2003 |
| JP | 2005-089655 A | 4/2005 |
| JP | 2006063242 A | 3/2006 |
| JP | 4095595 B2 | 6/2008 |
| JP | 2010-503586 A | 2/2010 |
| JP | 2011-212923 A | 10/2011 |
| JP | 2013-513716 A | 4/2013 |
| JP | 2014-016929 A | 1/2014 |
| JP | 2016050280 A | 4/2016 |
| RU | 2099260 C1 | 12/1997 |
| RU | 2104643 C1 | 2/1998 |
| RU | 2572039 C2 | 12/2015 |
| WO | WO-92/17382 A1 | 10/1992 |
| WO | WO-03/08180 A1 | 1/2003 |
| WO | WO-2004/085586 A2 | 10/2004 |
| WO | WO-2004/085600 A1 | 10/2004 |
| WO | WO-2004/111178 A1 | 12/2004 |
| WO | WO-2005/035382 A1 | 4/2005 |
| WO | WO-2006/020785 A1 | 2/2006 |
| WO | WO-2006/132680 A1 | 12/2006 |
| WO | WO-2006/132729 A1 | 12/2006 |
| WO | WO-2008/064014 A2 | 5/2008 |
| WO | WO-2008/087324 A2 | 7/2008 |
| WO | WO-2008/087424 A1 | 7/2008 |
| WO | WO-2009/098659 A1 | 8/2009 |
| WO | WO-2009/152031 A1 | 12/2009 |
| WO | WO-2011/061628 A1 | 5/2011 |
| WO | WO-2012/087821 A1 | 6/2012 |
| WO | WO-2014/026856 A1 | 2/2014 |
| WO | WO-2014/066339 A1 | 5/2014 |
| WO | WO-2014/151718 A2 | 9/2014 |
| WO | WO-2016/055346 A1 | 4/2016 |
| WO | WO-2016/061025 A1 | 4/2016 |
| WO | WO-2016/061053 A1 | 4/2016 |
| WO | WO-2016/061054 A1 | 4/2016 |
| WO | WO-2016/061069 A2 | 4/2016 |
| WO | WO-2017/136372 A1 | 8/2017 |
| WO | WO-2017/180888 A1 | 10/2017 |
| WO | WO-2017/218448 A1 | 12/2017 |
| WO | WO-2017/218449 A1 | 12/2017 |

OTHER PUBLICATIONS

International Search Report and Written Opinion, International Application No. PCT/US2017/037003, dated Aug. 22, 2017.
Kotake H et al: "Film used as packaging material, contains polyvinyl alcohol with preset copolymerization rate of vinyl unit containing anionic group, saponification degree and viscosity", WPI / Thomson, vol. 2006, No. 22, Mar. 9, 2006 (Mar. 9, 2006). XP002753313.
Maitra et al., Cross-Linking in Hydrogels—A Review, *American Journal of Polymer Science*, 4(2):25-31 (2014).
Muller et al. (eds.), Perfumes: Art, Science and Technology, Table of Contents and Copyright Pages, Springer Netherlands Publishing (1994).
Japanese Patent Application No. 2018-553422, Notice of Reasons for Refusal, dated Apr. 13, 2021.
All Office Actions, U.S. Appl. No. 15/620,860.
All Office Actions, U.S. Appl. No. 15/621,002.
All Office Actions, U.S. Appl. No. 15/486,613.
All Office Actions, U.S. Appl. No. 15/486,669.

* cited by examiner

WATER-SOLUBLE UNIT DOSE ARTICLES MADE FROM A COMBINATION OF DIFFERENT FILMS

CROSS-REFERENCE TO RELATED APPLICATIONS

This is a continuation of U.S. patent application Ser. No. 15/620,316, filed Jun. 12, 2017, which claims the benefit under 35 U.S.C. § 119(e) of U.S. Provisional Patent Application No. 62/349,655 filed Jun. 13, 2016. The entire disclosures of the foregoing applications are incorporated herein by reference.

Names of Parties to a Joint Research Agreement

The parties are MonoSol, LLC and Procter & Gamble Company.

FIELD

The present disclosure relates to water-soluble unit dose articles made from a combination of chemically different water-soluble films and optionally containing a composition, e.g. a household care composition or non-household care composition, that is at least partially enclosed by the water-soluble films in at least one compartment.

BACKGROUND

Water-soluble polymeric films are commonly used as packaging materials to simplify dispersing, pouring, dissolving and dosing of a material to be delivered. For example, water-soluble unit dose articles made from water-soluble film are commonly used to package household care compositions, e.g., a pouch containing a laundry or dish detergent, and non-household care compositions, e.g. a pouch containing a water treatment active agent. A user (e.g., a consumer) can directly add the water-soluble unit dose article to a mixing vessel, such as a bucket, sink or washing machine, or to the water tank of a toilet, or to a swimming pool. Advantageously, this provides for accurate dosing while eliminating the need for the consumer to measure the composition. The water-soluble unit dose article may also reduce mess that would be associated with dispensing a similar composition from a vessel, such as pouring a liquid laundry detergent from a bottle or dispensing water treatment granules or pellets from a bucket. The water-soluble unit dose article also insulates the composition therein from contact with the user's hands. In sum, water-soluble unit dose articles containing pre-measured agents provide for convenience of consumer use in a variety of applications.

Some water-soluble polymeric films that are used to make water-soluble unit dose articles will incompletely dissolve during a wash cycle, leaving film residue on items within the wash. Such problems may particularly arise when the water-soluble unit dose article is used under stressed wash conditions, such as when the pouch is used in cold water (e.g., water as low as 5° C. and/or up to 10° C. or 15° C.), with short water contact times, e.g. in a short wash cycle, and/or with low concentrations of water available for film dissolution, e.g. in a low-water wash cycle (e.g., wash liquors from about 3 L to about 20 L for pouches sized to contain 5 mL to 300 mL contents, for example). Notably, environmental concerns and energy cost are driving consumer desire for utilizing colder wash water and shorter wash cycles in laundry applications.

Some water-soluble polymeric films that are used to make water-soluble unit dose articles will completely dissolve during a wash cycle but are so substantive to water that the films will become sticky when exposed to high humidity conditions, causing water-soluble unit dose articles made thereof to stick together when exposed to such high humidity conditions during manufacturing or upon storage in the container during transport, at a warehouse or in consumers' home.

Additionally, it is desirable for the water-soluble unit dose article to have an adequate strength, both soon after making and upon storage, to withstand forces that may be applied during packing, transport, storage, and usage. Adequate strength may be particularly preferred with the pouches encapsulate liquid compositions, such as laundry detergent or dye concentrates, to avoid unintentional bursting and/or leakage.

There remains a need for water-soluble films and water-soluble unit dose articles, such as pouches, having the desired characteristics of good water solubility, reduced sticking, suitable pouch strength, chemical resistance, chemical and physical compatibility with laundry actives or other compositions in contact with the film or water-soluble unit dose article formed therefrom, and/or desirable mechanical properties, such as deformability upon thermo-forming and/or adequate sealing. It has been found that water-soluble unit dose articles according to the present disclosure exhibits optimal water solubility and reduced stickiness.

SUMMARY OF THE INVENTION

The present disclosure relates to a water-soluble unit dose article comprising at least one sealed compartment optionally comprising at least one composition (e.g. a household care composition or a non-household care composition), the water-soluble unit dose article comprising a first water soluble film and a second water soluble film, wherein the first film is sealed to the second film to form the at least one sealed compartment, wherein the first water-soluble film is chemically different from the second water soluble film with respect to the anionic content of the films.

The present disclosure also relates to methods of making and using such pouches.

BRIEF DESCRIPTION OF THE DRAWINGS

The figures herein are illustrative in nature and are not intended to be limiting.

DETAILED DESCRIPTION OF THE INVENTION

Definitions

Figure 1:
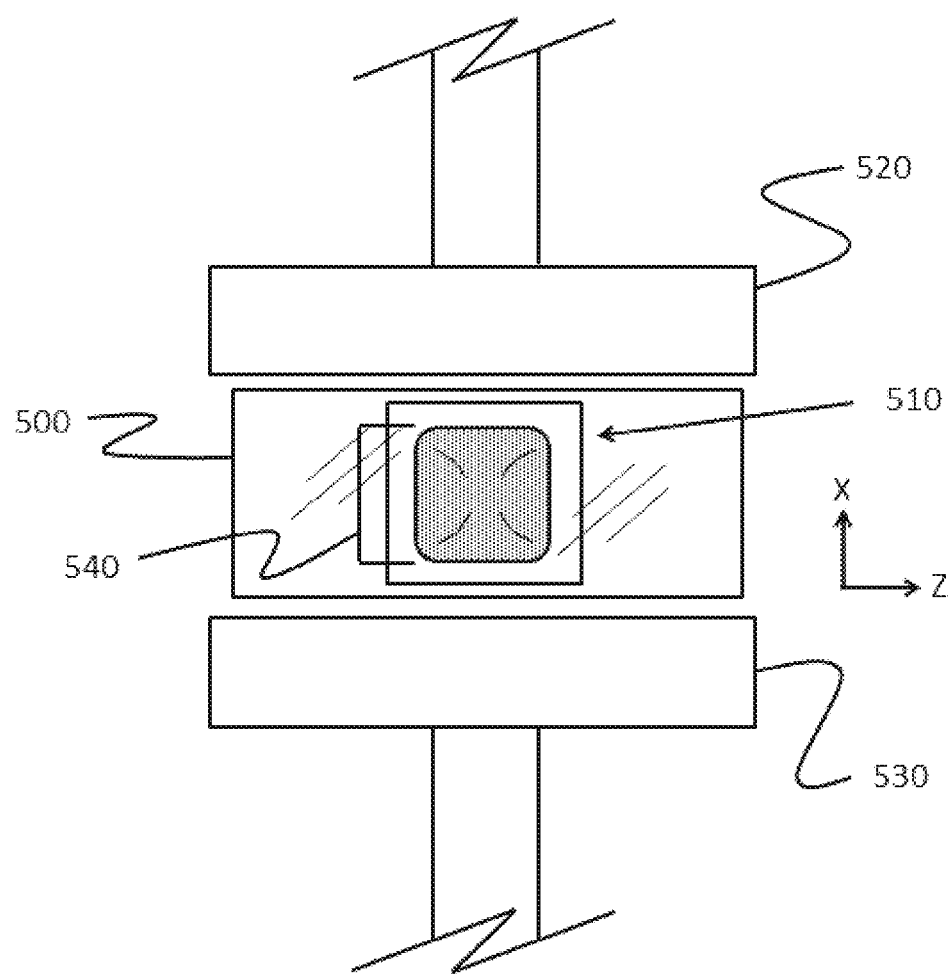
FIG. 1 shows a schematic illustration of the basic configuration of the unit dose article strength test and seal failure test.
Figure 2:
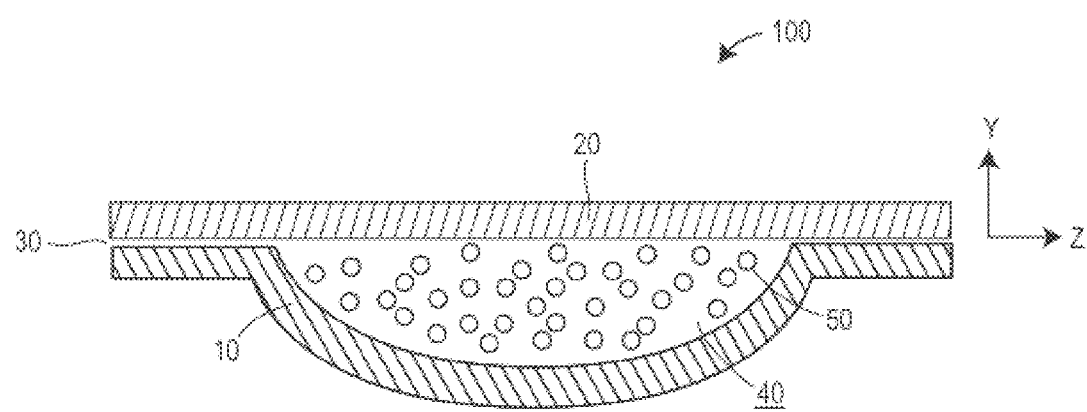
FIG. 2 shows a side cross-sectional view of a pouch.
Figure 3:
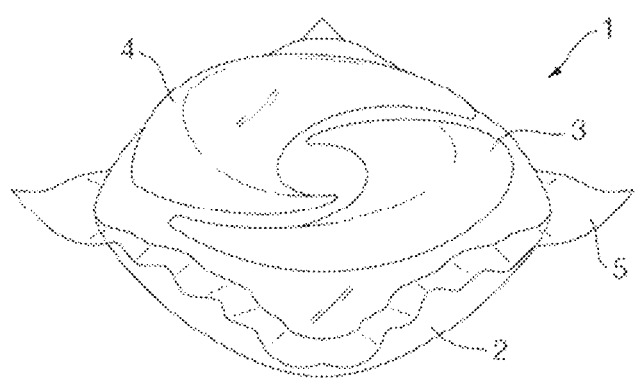
FIG. 3 shows a multi-compartment pouch.
Figure 4:
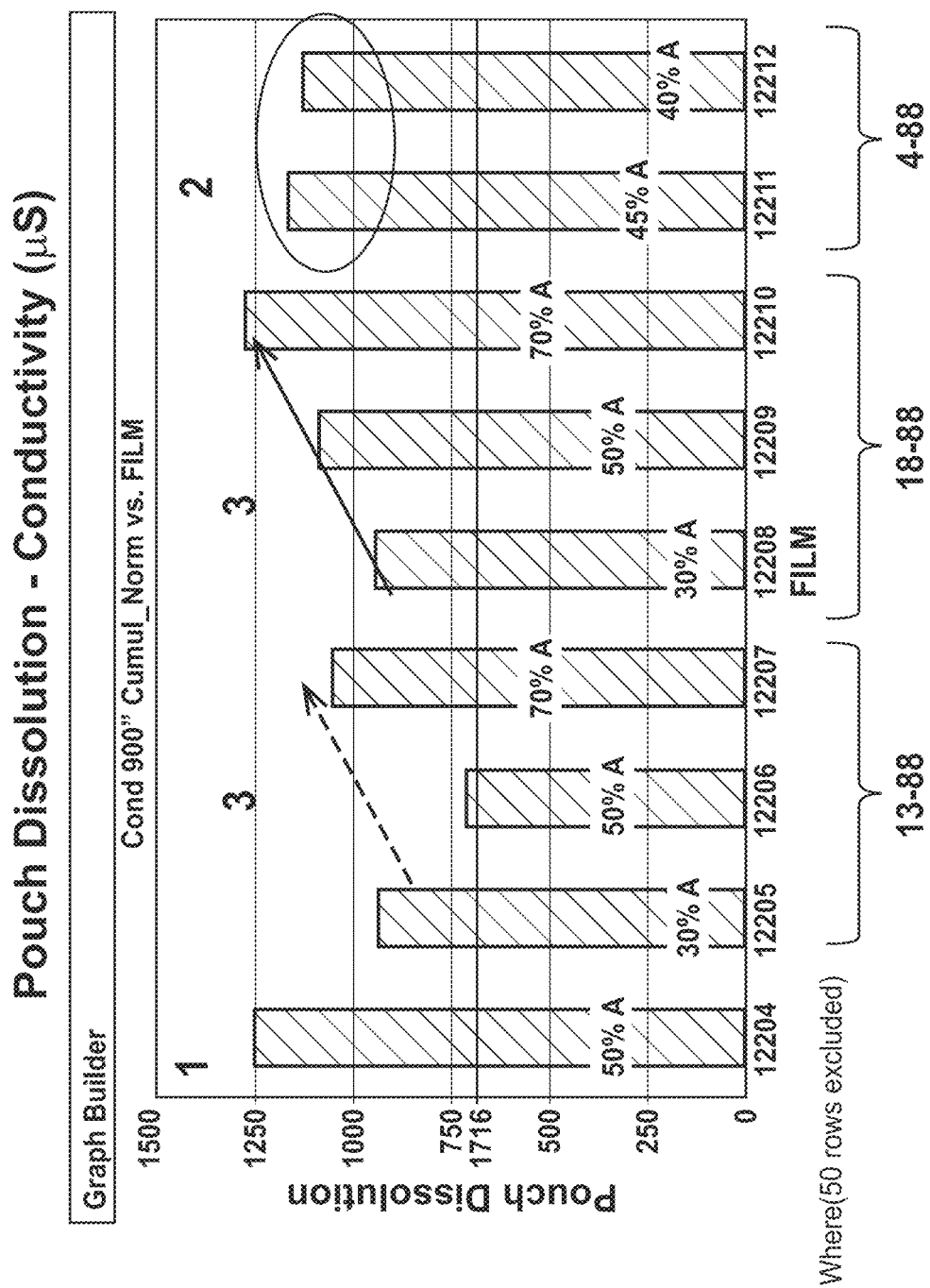
FIG. 4 shows a graph of the increased pouch dissolution of the unit dose articles as described herein.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

The water-soluble unit dose articles of the present disclosure include embodiments of packages themselves, and packages which may contain a composition, for example a household care composition or a non-household care composition. The composition can be selected from a liquid, solid or combination thereof. As used herein, "liquid" includes free-flowing liquids, as well as pastes, gels, foams and mousses. Non-limiting examples of liquids include light duty and heavy duty liquid detergent compositions, fabric enhancers, detergent gels commonly used for laundry, bleach and laundry additives. Gases, e.g., suspended bubbles, or solids, e.g. particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

As used herein, the term "homopolymer" generally includes polymers having a single type of monomeric repeating unit (e.g., a polymeric chain consisting of or consisting essentially of a single monomeric repeating unit). For the particular case of polyvinyl alcohol (PVOH), the term "homopolymer" (or "PVOH homopolymer" or "PVOH polymer") further includes copolymers having a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH homopolymer can include a true homopolymer having only vinyl alcohol units.

As used herein, the term "copolymer" generally includes polymers having two or more types of monomeric repeating units (e.g., a polymeric chain consisting of or consisting essentially of two or more different monomeric repeating units, whether as random copolymers, block copolymers, etc.). For the particular case of PVOH, the term "copolymer" (or "PVOH copolymer") further includes copolymers having a distribution of vinyl alcohol monomer units and vinyl acetate monomer units, depending on the degree of hydrolysis, as well as at least one other type of monomeric repeating unit (e.g., a ter- (or higher) polymeric chain consisting of or consisting essentially of vinyl alcohol monomer units, vinyl acetate monomer units, and one or more other monomer units, for example anionic monomer units). In the limiting case of 100% hydrolysis, a PVOH copolymer can include a copolymer having vinyl alcohol units and one or more other monomer units, but no vinyl acetate units.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C., under atmospheric pressure, and at 50% relative humidity.

In the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

It is expressly contemplated that for any number value described herein, e.g. as a parameter of the subject matter described or part of a range associated with the subject matter described, an alternative which forms part of the description is a functionally equivalent range surrounding the specific numerical value (e.g. for a dimension disclosed as "40 mm" an alternative embodiment contemplated is "about 40 mm").

Water-Soluble Unit Dose Article

The water-soluble unit dose article described herein comprises a first water-soluble film and a second water-soluble film shaped such that the unit-dose article comprises at least one internal compartment surrounded by the water-soluble films. The water-soluble films are sealed to one another such to define the internal compartment, and in a completed, filled article the films are sealed to one another such that that the detergent or other composition does not leak out of the compartment during storage. However, upon addition of the water-soluble unit dose article to water (or vice-vera), the water-soluble film dissolves and releases the contents of the internal compartment, e.g. into the water or wash liquor. The water-soluble unit dose article may be a pouch.

The area in which the two films meet and are sealed together is referred to as the seal area. Often, the seal area comprises a 'skirt' or 'flange' which comprises area of the first water-soluble film sealed to an area of the second water-soluble film and which generally protrudes out from the main body of the unit dose article. A preferred method of making a unit dose article is described in more detail below.

The compartment should be understood as meaning a closed internal space within the unit dose article, which can hold a detergent or other composition. During manufacture, the first water-soluble film according to the present invention may be shaped to comprise an open compartment into which the detergent or other composition is added. The second water-soluble film according to the present invention is then laid over the first film in such an orientation as to close the opening of the compartment. The first and second films are then sealed together along a seal region.

The unit dose article may comprise more than one compartment, even at least two compartments, or even at least three compartments. The compartments may be arranged in superposed orientation, i.e. one positioned on top of the other. In such an orientation the unit dose article will comprise three films, top, middle and bottom. Preferably, the middle film will correspond to the second water-soluble film according to the present invention and top and bottom films will correspond to the first water-soluble film according to the present invention. Alternatively, the compartments may be positioned in a side-by-side orientation, i.e. one orientated next to the other. The compartments may even be orientated in a 'tyre and rim' arrangement, i.e. a first compartment is positioned next to a second compartment, but the first compartment at least partially surrounds the second compartment, but does not completely enclose the second compartment. Alternatively one compartment may be completely enclosed within another compartment. In such a multicompartment orientation, the first water-soluble film according to the present invention may be shaped to comprise an open compartment into which the detergent or other composition is added. The second water-soluble film according to the present invention is then laid over the first film in such an orientation as to close the opening of the compartment.

Wherein the unit dose article comprises at least two compartments, one of the compartments may be smaller than the other compartment. Wherein the unit dose article comprises at least three compartments, two of the compartments may be smaller than the third compartment, and preferably the smaller compartments are superposed on the larger compartment. The superposed compartments preferably are orientated side-by-side.

In a multi-compartment orientation, a composition (e.g. a non-household care composition) may be comprised in at least one of the compartments. It may, for example, be comprised in just one compartment, or may be comprised in two compartments, or even in three compartments. For example, in a multi-compartment orientation, the detergent composition according to the present invention may be comprised in at least one of the compartments. Alternatively the detergent may, for example, be comprised in just one compartment, or may be comprised in two compartments, or even in three compartments Each compartment may comprise the same or different compositions. The different compositions could all be in the same form, or they may be in different forms.

The water-soluble unit dose article may comprise at least two internal compartments, wherein a liquid composition is comprised in at least one of the compartments, preferably wherein the unit dose article comprises at least three compartments, wherein the liquid composition is comprised in at least one of the compartments. For example, a water-soluble unit dose detergent article may comprise at least two internal compartments, wherein the liquid laundry detergent composition is comprised in at least one of the compartments, preferably wherein the unit dose article comprises at least three compartments, wherein the detergent composition is comprised in at least one of the compartments.

First and Second Water-Soluble Films

The water-soluble unit dose article comprises a first water-soluble film and a second water-soluble film and the first water-soluble film and the second water-soluble film are chemically different to one another.

For the avoidance of doubt, in the context of the present invention 'chemically different' herein means where the 'virgin films', i.e. films received from the supplier/manufacture and prior to unwinding on a unit dose article making unit, having at least one substance present in at least one of the film compositions that differentiates the first from the second film composition and impacts at least one of the physical properties of the film, such as water capacity, elongation modulus, and tensile strength at break, per the test method(s) described herein, rendering this at least one physical film property different between the first and second films. Varying chemical compositions of films due to natural making processes i.e. batch to batch variations are as such not considered chemically different films within the scope of this invention.

Non limiting examples of chemically differentiating substances include use of different polymer target resins and or content, different plasticizer composition and or content or different surfactant and or content. Water soluble unit dose articles comprising films solely differing in physical properties but having the same substance content, such as films solely differing in film thickness, are considered outside the scope of this invention. Unit dose articles made from films being solely differentiated through the presence versus the absence of a coating layer are also considered outside the scope of the invention.

Preferably, the first water-soluble film is thermoformed during manufacture of the unit dose article. By 'thermoforming' we herein mean that the film is heated prior to deformation, for example, by passing the film under an infrared lamp, the deformation step preferably being enabled by laying the water soluble film over a cavity and applying vacuum or an under pressure inside the cavity under the film. The second water-soluble film may be thermoformed during manufacture of the unit dose article. Alternatively the second water-soluble film may not be thermoformed during manufacture of the unit dose article. Preferably, the first water-soluble film is thermoformed during manufacture of the unit dose article and the second water-soluble film is not thermoformed during manufacture of the unit dose article.

The first water-soluble film and the second water-soluble film each may independently have a thickness before incorporation into the unit dose article of between 40 microns and 100 microns, preferably between 60 microns and 90 microns, more preferably between 70 microns and 80 microns.

Preferably the difference in thickness before incorporation into the unit dose article between the first water-soluble film and the second water-soluble film is less than 50%, preferably less than 30%, more preferably less than 20%, even more preferably less than 10%, or the thicknesses may be equal.

The first water-soluble film and the second water-soluble film according to the invention are preferably single layer films, more preferably manufactured via solution casting.

The water-soluble film can further have a residual moisture content of at least 4 wt. %, for example in a range of about 4 to about 10 wt. %, as measured by Karl Fischer titration.

The first water-soluble film and/or the second water-soluble film described herein may contain polymers, e.g., PVOH polymers, which comprise anionic monomer units. The amount of anionic monomer units present in the first water-soluble film and/or the second water-soluble film may be expressed in terms of anionic content. The first water-soluble film may have a first anionic content and the second water-soluble film may have a second anionic content. The first anionic content may be different from the second anionic content. By "anionic content" it is meant the anionic monomer units present in the PVOH polymer of the film, for example as molar content (mol. %) of the anionic monomer units compared to the total amount of PVOH polymer in the film (e.g., total of PVOH polymer, including homopolymer(s) and copolymer(s)). The amount of anionic monomer units may be characterized in terms of the molar content (expressed, e.g., as mol. %) of the anionic monomer units in a polymer, e.g., a PVOH copolymer. The one or more anionic monomer units may be present in the PVOH copolymer in an amount in a range of from about 1 mol. % to about 10 mol. %, or from about 2 mol. % to about 8 mol. %, or from about 2 mol % to about 6 mol %, or from about 3 mol % to about 6 mol %, or from about 1 mol % to about 4 mol %, or from about 3 mol % to about 5 mol %, or from about 3.5 mol. % to about 4.5 mol %, or from about 4 mol. % to about 4.5 mol. %, individually or collectively. The anionic monomer unit(s) may be present in the PVOH copolymer in an amount of at least about 3.0 mol %, at least about 3.5 mol. %, at least about 4.0 mol. %, and/or up to about 6.0 mol %, up to about 5.5 mol %, up to about 5.0 mol %, or up to about 4.5 mol. %.

The water-soluble unit dose article disclosed herein may comprise a first water soluble film comprising a first anionic content and a second water soluble film comprising a second anionic content, where the first anionic content is greater than the second anionic content. The difference between the first anionic content and the second anionic content is about 0.05 mol % to about 4 mol %, or about 0.1 mol % to about 2 mol %, or about 0.2 mol % to about 1 mol %. The first anionic content may comprise a first type of anionic monomer unit and the second anionic content may comprise a second type of anionic monomer unit.

The first water-soluble film and the second water-soluble film may independently comprise from about 0 mol. % to about 10 mol. % of anionic monomer unit(s) compared to the total amount of PVOH polymer in the film. The first water-soluble film and the second water-soluble film may independently comprise at least about 0.25 mol. %, at least about 0.5 mol. %, at least about 0.75 mol. %, at least about 1.0 mol. %, at least about 1.25 mol. %, or at least about 1.5 mol. % and/or up to about 7.5 mol. %, up to about 5.0 mol. %, up to about 4.0 mol. %, up to about 3.0 mol. %, up to about 2.0 mol. %, or up to about 1.5 mol. % of anionic monomer unit(s) compared to the total amount of PVOH polymer in the film. For example, for a film comprising a 50 wt %/50 wt % blend of two PVOH polymers, where the first PVOH polymer is a copolymer that includes 4 mol. % anionic monomer units and the second PVOH polymer is a homopolymer, the anionic content is about 2.0 mol. % of total PVOH polymer. Or, for example, for a film comprising a 50 wt %/50 wt % blend of two PVOH polymers, where the first PVOH polymer is a copolymer that includes 4 mol. % anionic monomer units and the second PVOH polymer is a copolymer that includes 2 mol. % anionic monomer units, the anionic content is about 3.0 mol. % of total PVOH polymer. Or, for example, for a film comprising a 100 wt % of a PVOH copolymer that includes 4 mol. % anionic monomer units, the anionic content is about 4.0 mol. % of total PVOH polymer.

Thus, for a film comprising a blend of two PVOH polymers, where the first PVOH polymer is a copolymer that includes anionic monomer units and the second PVOH polymer is a homopolymer, the anionic content of the film may be increased by increasing the mol. % anionic monomer units in the copolymer or increasing the wt % of copolymer in the copolymer/homopolymer blend.

The PVOH copolymer can include two or more types of anionic monomer units. Preferably, the PVOH copolymer includes a single type of anionic monomer unit.

The anionic monomer unit may be selected from the group consisting of anionic monomers derived from of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts thereof, esters thereof, and combinations thereof;

Preferably, the anionic monomer unit is selected from the group consisting of anionic monomers derived from maleic acid, monoalkyl maleate, dialkyl maleate, maleic anhydride, alkali metal salts thereof, esters thereof, and combinations thereof;

More preferably the anionic monomer unit is selected from the group consisting of anionic monomers derived from maleic acid, monomethyl maleate, dimethyl maleate, maleic anyhydride, alkali metal salts thereof, esters thereof, and combinations thereof.

The first water soluble film may comprise a first water soluble resin and the second water soluble film may comprise a second water soluble resin. The first water soluble resin may be chemically different from the second water soluble resin. Preferably, the first water soluble resin comprises at least one polyvinyl alcohol homopolymer or at least one polyvinyl alcohol copolymer or a blend thereof and the second water soluble resin comprises at least one polyvinyl alcohol homopolymer or at least one polyvinyl alcohol copolymer or a blend thereof, provided that at least one of the first water-soluble resin or the second water-soluble resin comprises at least one polyvinyl alcohol copolymer comprising an anionic monomer unit.

The first water soluble resin may comprise a blend of a polyvinyl alcohol homopolymer and a polyvinyl alcohol copolymer comprising an anionic monomer unit, optionally wherein the blend comprises from 0% to 70% by weight of the first water soluble resin of the polyvinyl alcohol copolymer comprising an anionic monomer unit and from 30% to about 100% by weight of the first water soluble resin of the polyvinyl alcohol homopolymer. The blend can comprise from 10% to 70%, or from 15% to about 65%, or from 20% to 50%, or from 30% to 40% of the polyvinyl alcohol copolymer comprising an anionic monomer unit, based on the total weight of the first water soluble resin. In another type of embodiment, the blend comprises 65 wt. % or greater of an anionic polyvinyl alcohol copolymer, or greater than 65 wt. % of an anionic polyvinyl alcohol copolymer.

The second water soluble resin may comprise a blend of a polyvinyl alcohol homopolymer and a polyvinyl alcohol copolymer comprising an anionic monomer unit, optionally wherein the blend comprises from 0% to 70% of the polyvinyl alcohol copolymer comprising an anionic monomer unit and from 30% to 100% of the polyvinyl alcohol homopolymer, based on the total weight of the second water soluble resin in the film. The blend can comprise from 10% to 70%, or from 15% to 65%, or from 20% to 50%, or from 30% to 40% of the polyvinyl alcohol copolymer comprising an anionic monomer unit, based on the total weight of the second water soluble resin in the film. In another type of embodiment, the blend comprises 65 wt. % or greater of an anionic polyvinyl alcohol copolymer, or greater than 65 wt. % of an anionic polyvinyl alcohol copolymer.

The first water soluble resin and the second water soluble resin may also comprise different polyvinyl alcohol copolymers comprising anionic monomer units.

Preferably, the at least one polyvinyl alcohol homopolymer or the at least one polyvinyl alcohol copolymer or the blend thereof of the first water-soluble film and the at least one polyvinyl alcohol homopolymer or the at least one polyvinylalcohol copolymer or the blend thereof of the second water-soluble film independently have a 4% solution viscosity in demineralized water at 25° C. in a range of 4 cP to 40 cP, preferably of 10 cP to 30 cP, more preferably of 11 cP to 26 cP. More preferably, the first water soluble resin comprises at least one polyvinyl alcohol homopolymer or at least one polyvinylalcohol copolymer or a blend thereof having a 4% solution viscosity in demineralized water at 25° C. in a range of about 8 cP to about 40 cP, or about 12 cP to about 30 cP, or about 14 cP to about 26 cP and the second water soluble resin comprises at least one polyvinyl alcohol homopolymer or at least one polyvinylalcohol copolymer or a blend thereof having a 4% solution viscosity in demineralized water at 25° C. in a range of about 4 cP to about 35 cP, or about 10 cP to about 20 cP, or about 10 cP to about 15 cP, or about 11 cP to about 14 cP.

Preferably, the 4% solution viscosity in demineralized water at 25° C. of the at least one polyvinyl alcohol homopolymer or the at least one polyvinylalcohol copolymer or the blend thereof of the first water soluble resin is greater than the 4% solution viscosity in demineralized water at 25° C. of the at least one polyvinyl alcohol homopolymer or the at least one polyvinylalcohol copolymer or the blend thereof of the second water soluble resin. More preferably, the difference between the 4% solution viscosity in demineralized water at 25° C. of the at least one polyvinyl alcohol homopolymer or the at least one polyvinylalcohol copolymer or the blend thereof of the first water soluble resin and the 4% solution viscosity in demineralized water at 25° C. of the at least one polyvinyl alcohol homopolymer or the at least one polyvinylalcohol copolymer or the blend thereof of the second water soluble resin is about 2 cP about 20 cP, or about 3 cP to about 15 cP, or about 4 cP to about 12 cP.

By 'difference' we herein mean the difference in the value of the 4% solution viscosity in demineralized water at 25° C. of the at least one polyvinyl alcohol homopolymer or the at least one polyvinylalcohol copolymer or the blend thereof of the first water soluble resin and the value of the 4% solution viscosity in demineralized water at 25° C. of the at least one polyvinyl alcohol homopolymer or the at least one polyvinylalcohol copolymer or the blend thereof of the second water soluble resin.

When the first water-soluble resin and the second water-soluble resin each comprises a blend of a polyvinyl alcohol homopolymer and a polyvinyl alcohol copolymer comprising an anionic monomer unit, the polyvinyl alcohol copolymer comprising an anionic monomer unit of the first water-soluble resin may have a first viscosity ($\mu_{c1}$); the polyvinyl alcohol copolymer comprising an anionic monomer unit of the second water-soluble resin may have a second viscosity ($\mu_{c2}$); the polyvinyl alcohol homopolymer of the first water-soluble resin may have a first viscosity ($\mu_{h1}$); the polyvinyl alcohol homopolymer of the second water-soluble resin may have a second viscosity ($\mu_{h2}$); the first water-soluble resin may have a blend viscosity ($\mu_{blend1}$); and the second water-soluble resin may have a blend viscosity ($\mu_{blend2}$). Blend viscosities are weight averaged and may be calculated as follows: blend viscosity=$e\char`\^(w_1(\ln \mu_{c1})+w_2(\ln \mu_{h1}))$, where e is Euler's number and w is weight % based on the total weight of the respective water soluble resin. And, the viscosity difference may be calculated in a number of ways:

$$|\mu_{c1}-\mu_{c2}|>0, \text{ when } \mu_{h2}=\mu_{h1}; \quad \text{(i)}$$

$$|\mu_{h1}-\mu_{h2}|>0, \text{ when } \mu_{c2}=\mu_{c1}; \quad \text{(ii)}$$

$$|\mu_{blend1}-\mu_{blend2}|>0. \quad \text{(iii)}$$

Preferably, the first polyvinyl alcohol homopolymer and second polyvinyl alcohol homopolymer and the first polyvinyl alcohol copolymer and second polyvinyl alcohol copolymer independently have a degree of hydrolysis of from 80% to 99% preferably from 85% to 95% more preferably from 87% and 93%.

Preferably, the first water-soluble film and the second water-soluble film independently have a water soluble resin content of between 30% and 90%, more preferably between 40% and 80%, even more preferably between 50% and 75%, most preferably between 60% and 70% by weight of the film.

Other water soluble polymers for use in addition to the first polyvinyl alcohol homopolymers and second polyvinyl alcohol homopolymer and first polyvinyl alcohol copolymer and second polyvinyl alcohol copolymer can include, but are not limited to a vinyl alcohol-vinyl acetate copolymer, sometimes referred to as a PVOH homopolymer, polyacrylates, water-soluble acrylate copolymers, polyvinyl pyrrolidone, polyethyleneimine, pullulan, water-soluble natural polymers including, but not limited to, guar gum, gum Acacia, xanthan gum, carrageenan, and starch, water-soluble polymer derivatives including, but not limited to, modified starches, ethoxylated starch, hydroxyethylated starch and hydroxypropylated starch, copolymers of the forgoing and combinations of any of the foregoing. Yet other water-soluble polymers can include polyalkylene oxides, polyacrylamides, polyacrylic acids and salts thereof, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, polymethacrylates, and combinations of any of the foregoing. Such water-soluble polymers, whether PVOH or otherwise are commercially available from a variety of sources.

The first water-soluble film has a first water capacity, and the second water-soluble film has a second water capacity wherein the first water capacity is less than the second water capacity.

The difference between the water capacity of the first water soluble film and the second water-soluble film is between 0.01% and 1%, preferably from 0.03% to 0.5%, most preferably from 0.05% to 0.3%. The first water-soluble film and the second water-soluble film are described in more detail below. By 'difference' we herein mean the difference in the value of the first water capacity and the value of the second water capacity. By 'water capacity' we herein mean the capacity of the film to absorb water over a fixed period of time at a particular relative humidity and temperature, measured as a mass increase of the film being tested. The method for measuring water capacity is described in more detail below.

Preferably, the first water-soluble film has a water capacity from 1% to 10%, more preferably from 2% to 8%, most preferably from 3% to 6%.

Preferably, the second water-soluble film has a water capacity from 1.5% to 12%, more preferably from 2.5% to 10%, most preferably from 3.5% to 8%.

The first water-soluble film may have a first tensile strain at break of between 300% and 1600%, preferably between 400% and 1200%, more preferably between 600% and 1200%. The method to determine tensile strain at break is described in more detail below.

The second water-soluble film may have a second tensile strain at break of between 300% and 1200%, preferably between 500% and 1000%, more preferably between 500% and 1000%. By tensile strain at break we herein mean the ability of the film, pre-equilibrated with the composition which it will contain, e.g. a detergent composition contacting the film in a unit dose article comprising said film and detergent or other composition, to elongate prior to breaking when a stress is applied. The method to determine tensile strain at break is described in more detail below.

The difference between the first tensile strain at break and the second tensile strain at break may be from 10% to 1000%, preferably from 100% to 750%, more preferably from 200% to 500%. By 'difference in tensile strain at break' we herein mean the difference in the value of the first tensile strain at break and the value of the second tensile strain at break.

Preferably, the first water soluble film has a first elongation modulus, the second water soluble film has a second elongation modulus, the first elongation modulus is greater than the second elongation modulus, and the difference between the first elongation modulus and the second elongation modulus is from a 0.5 MPa to 10 MPa, preferably from 1 MPa to 8 MPa, more preferably from 2 MPa to 7 MPa.

By 'difference' we herein mean the difference in the value of the first elongation modulus and the value of the second elongation modulus. By 'elongation modulus' we herein mean the ability of the film to be elongated when a stress is applied. The method for measuring elongation modulus is described in more detail below.

Preferably, the first elongation modulus is from 1 MPa to 20 MPa, more preferably from 3 MPa to 20 MPa.

Preferably, the second elongation modulus is from 1 MPa to 15 MPa, more preferably from 3 MPa to 15 MPa.

Preferably, the water-soluble unit dose article exhibits a dissolution profile, according to the unit dose article dose article machine wash dissolution test method described below of less than 6.2 preferably less than 6 more preferably less than 5.8.

The first and or second film may independently be opaque, transparent or translucent. The first and or second film may independently comprise a printed area. The printed area may cover between 10 and 80% of the surface of the film; or between 10 and 80% of the surface of the film that is in contact with the internal space of the compartment; or between 10 and 80% of the surface of the film and between 10 and 80% of the surface of the compartment.

The area of print may cover an uninterrupted portion of the film or it may cover parts thereof, i.e. comprise smaller areas of print, the sum of which represents between 10 and 80% of the surface of the film or the surface of the film in contact with the internal space of the compartment or both.

The area of print may comprise inks, pigments, dyes, blueing agents or mixtures thereof. The area of print may be opaque, translucent or transparent.

The area of print may comprise a single colour or maybe comprise multiple colours, even three colours. The area of print may comprise white, black, blue, red colours, or a mixture thereof. The print may be present as a layer on the surface of the film or may at least partially penetrate into the film. The film will comprise a first side and a second side. The area of print may be present on either side of the film, or be present on both sides of the film. Alternatively, the area of print may be at least partially comprised within the film itself.

The area of print may be achieved using standard techniques, such as flexographic printing or inkjet printing. Preferably, the area of print is achieved via flexographic printing, in which a film is printed, then moulded into the shape of an open compartment. This compartment is then filled with a detergent or other composition and a second film placed over the compartment and sealed to the first film. The area of print may be on either or both sides of the film.

Alternatively, an ink or pigment may be added during the manufacture of the film such that all or at least part of the film is coloured.

The first and or second film may independently comprise an aversive agent, for example a bittering agent. Suitable bittering agents include, but are not limited to, naringin, sucrose octaacetate, quinine hydrochloride, denatonium benzoate, or mixtures thereof. Any suitable level of aversive agent may be used in the film. Suitable levels include, but are not limited to, 1 to 5000 ppm, or even 100 to 2500 ppm, or even 250 to 2000 ppm.

The first and/or second film may also comprise other secondary ingredient typically known by a skilled person in the art such as, but not limited to, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. Embodiments including plasticizers are preferred. The amount of such agents can be up to about 50 wt. %, 20 wt %, 15 wt %, 10 wt %, 5 wt. %, 4 wt % and/or at least 0.01 wt. %, 0.1 wt %, 1 wt %, or 5 wt %, individually or collectively.

The plasticizer can include, but is not limited to, glycerin, diglycerin, sorbitol, ethylene glycol, diethylene glycol, triethylene glycol, dipropylene glycol, tetraethylene glycol, propylene glycol, polyethylene glycols up to 400 MW, neopentyl glycol, trimethylolpropane, polyether polyols, sorbitol, 2-methyl-1,3-propanediol (MPDiol®), ethanolamines, and a mixture thereof. A preferred plasticizer is glycerin, sorbitol, triethyleneglycol, propylene glycol, dipropylene glycol, 2-methyl-1,3-propanediol, trimethylolpropane, or a combination thereof. The total amount of the plasticizer can be in a range of about 10 wt. % to about 45 wt. %, or about 15 wt. % to about 35 wt. %, or about 20 wt. % to about 30 wt. %, or about 20 wt. % to about 45 wt. %, for example about 25 wt. %, based on total film weight. In embodiments, the amount of plasticizer in the water-soluble film is expressed in parts per 100 parts total water soluble polymer (PHR) in the water-soluble film and is present at least 30 PHR, or at least 35 PHR, for example. The total amount of plasticizer can be up to 40 PHR or 45 PHR or 50 PHR, for example. The total amount of plasticizer can be in a range of 30-50 PHR, about 32.5 PHR to about 42.5 PHR, or 35-45 PHR, or 35-40 PHR, or greater than 30 PHR and less than 45 PHR, or 40 PHR to 50 PHR, for example. The total amount of plasticizer can be 34 or 37.5 PHR.

Surfactants for use in water-soluble films are well known in the art. Optionally, surfactants are included to aid in the dispersion of the resin solution upon casting. Suitable surfactants can include the nonionic, cationic, anionic and zwitterionic classes. Suitable surfactants include, but are not limited to, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof. In embodiments, the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof.

In various embodiments, the amount of surfactant in the water-soluble film is in a range of about 0.1 wt % to about 8.0 wt %, or about 1.0 wt % to about 7.0 wt %, or about 3 wt % to about 7 wt %, or about 5 wt % to about 7 wt %. In embodiments, the amount of surfactant in the water-soluble film is expressed in parts per 100 parts total water soluble polymer (phr) in the water-soluble film and is present in a range of about 0.5 phr to about 12 phr, about 1.0 phr to about 11.0 phr, about 3.0 phr to about 10.5 phr, or about 1.0 phr to about 2.0 phr.

Suitable lubricants/release agents can include, but are not limited to, fatty acids and their salts, fatty alcohols, fatty esters, fatty amines, fatty amine acetates and fatty amides. Preferred lubricants/release agents are fatty acids, fatty acid salts, and fatty amine acetates. In one type of embodiment, the amount of lubricant/release agent in the water-soluble film is in a range of about 0.02 wt % to about 1.5 wt %, optionally about 0.1 wt % to about 1 wt %.

Suitable fillers/extenders/antiblocking agents/detackifying agents include, but are not limited to, starches, modified starches, crosslinked polyvinylpyrrolidone, crosslinked cellulose, microcrystalline cellulose, silica, metallic oxides, calcium carbonate, talc, mica, stearic acid and metal salts thereof, for example, magnesium stearate. Preferred materials are starches, modified starches and silica. In one type of embodiment, the amount of filler/extender/antiblocking agent/detackifying agent in the water soluble film can be in a range of about 1 wt. % to about 6 wt. %, or about 1 wt. % to about 4 wt. %, or about 2 wt. % to about 4 wt. %, or about 1 phr to about 6 phr, or about 1 phr to about 4 phr, or about 2 phr to about 4 phr, for example.

An anti-block agent (e.g. $SiO_2$ and/or stearic acid)) can be present in the film in an amount of at least 0.1 PHR, or at least 0.5 PHR, or at least 1 PHR, or in a range of about 0.1 to 5.0 PHR, or about 0.1 to about 3.0 PHR, or about 0.4 to 1.0 PHR, or about 0.5 to about 0.9 PHR, or about 0.5 to about 2 PHR, or about 0.5 to about 1.5 PHR, or 0.1 to 1.2 PHR, or 0.1 to 4 PHR, for example 0.5 PHR, 0.6 PHR, 0.7 PHR, 0.8 PHR, or 0.9 PHR.

If the anti-block agent is an $SiO_2$ particle, a suitable median particle size for the anti-block agent includes a median size in a range of about 3 or about 4 microns to about 11 microns, or about 4 to about 8 microns, or about 5 to about 6 microns, for example 5, 6, 7, 8, or 8 microns. A suitable $SiO_2$ is an untreated synthetic amorphous silica designed for use in aqueous systems.

Detergent Composition

The detergent composition may be in the form of free flowing powder, a liquid, a compacted solid, a gel or a mixture thereof.

The detergent composition may be in the form of a free flowing powder. Such a free flowing powder may have an average particle size diameter of between 100 microns and 1500 microns, preferably between 100 microns and 1000 microns, more preferably between 100 microns and 750 microns. Those skilled in the art will be aware of standard techniques to measure particle size. The detergent composition may be a free flowing laundry detergent composition.

The detergent composition may be a liquid. In relation to the liquid detergent composition of the present invention, the term 'liquid' encompasses forms such as dispersions, gels, pastes and the like. The liquid composition may also include gases in suitably subdivided form. However, the liquid composition excludes forms which are non-liquid overall, such as tablets or granules.

The detergent composition may be a liquid laundry detergent composition. The term 'liquid laundry detergent composition' refers to any laundry detergent composition comprising a liquid capable of wetting and treating fabric e.g., cleaning clothing in a domestic washing machine.

The laundry detergent composition is used during the main wash process but may also be used as pre-treatment or soaking compositions.

Laundry detergent compositions include fabric detergents, fabric softeners, 2-in-1 detergent and softening, pre-treatment compositions and the like.

The laundry detergent composition may comprise an ingredient selected from bleach, bleach catalyst, dye, hueing dye, brightener, cleaning polymers including alkoxylated polyamines and polyethyleneimines, soil release polymer, surfactant, solvent, dye transfer inhibitors, chelant, builder, enzyme, perfume, encapsulated perfume, polycarboxylates, rheology modifiers, structurant, hydrotropes, pigments and dyes, opacifiers, preservatives, anti-oxidants, processing aids, conditioning polymers including cationic polymers, antibacterial agents, pH trimming agents such as hydroxides and alkanolamines, suds suppressors, and mixtures thereof.

Surfactants can be selected from anionic, cationic, zwitterionic, non-ionic, amphoteric or mixtures thereof. Preferably, the fabric care composition comprises anionic, non-ionic or mixtures thereof.

The anionic surfactant may be selected from linear alkyl benzene sulfonate, alkyl ethoxylate sulphate and combinations thereof.

Suitable anionic surfactants useful herein can comprise any of the conventional anionic surfactant types typically used in liquid detergent products. These include the alkyl benzene sulfonic acids and their salts as well as alkoxylated or non-alkoxylated alkyl sulfate materials.

The non-ionic surfactant may be selected from fatty alcohol alkoxylate, an oxo-synthesised fatty alcohol alkoxylate, Guerbet alcohol alkoxylates, alkyl phenol alcohol alkoxylates or a mixture thereof. Suitable nonionic surfactants for use herein include the alcohol alkoxylate nonionic surfactants. Alcohol alkoxylates are materials which correspond to the general formula: $R^1(C_mH_{2m}O)_nOH$ wherein $R^1$ is a $C_8$-$C_{16}$ alkyl group, m is from 2 to 4, and n ranges from about 2 to 12. In one aspect, $R^1$ is an alkyl group, which may be primary or secondary, that comprises from about 9 to 15 carbon atoms, or from about 10 to 14 carbon atoms. In one aspect, the alkoxylated fatty alcohols will also be ethoxylated materials that contain on average from about 2 to 12 ethylene oxide moieties per molecule, or from about 3 to 10 ethylene oxide moieties per molecule.

The shading dyes employed in the present laundry detergent compositions may comprise polymeric or non-polymeric dyes, pigments, or mixtures thereof. Preferably the shading dye comprises a polymeric dye, comprising a chromophore constituent and a polymeric constituent. The chromophore constituent is characterized in that it absorbs light in the wavelength range of blue, red, violet, purple, or combinations thereof upon exposure to light. In one aspect, the chromophore constituent exhibits an absorbance spectrum maximum from about 520 nanometers to about 640 nanometers in water and/or methanol, and in another aspect, from about 560 nanometers to about 610 nanometers in water and/or methanol.

Although any suitable chromophore may be used, the dye chromophore is preferably selected from benzodifuranes, methine, triphenylmethanes, napthalimides, pyrazole, napthoquinone, anthraquinone, azo, oxazine, azine, xanthene, triphenodioxazine and phthalocyanine dye chromophores. Mono and di-azo dye chromophores are preferred.

The dye may be introduced into the detergent composition in the form of the unpurified mixture that is the direct result of an organic synthesis route. In addition to the dye polymer therefore, there may also be present minor amounts of un-reacted starting materials, products of side reactions and mixtures of the dye polymers comprising different chain lengths of the repeating units, as would be expected to result from any polymerisation step.

The laundry detergent compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

The laundry detergent compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof.

The composition may comprise a brightener. Suitable brighteners are stilbenes, such as brightener 15. Other suitable brighteners are hydrophobic brighteners, and brightener 49. The brightener may be in micronized particulate form, having a weight average particle size in the range of from 3 to 30 micrometers, or from 3 micrometers to 20 micrometers, or from 3 to 10 micrometers. The brightener can be alpha or beta crystalline form.

The compositions herein may also optionally contain one or more copper, iron and/or manganese chelating agents. The chelant may comprise 1-hydroxyethanediphosphonic acid (HEDP) and salts thereof; N,N-dicarboxymethyl-2-aminopentane-1,5-dioic acid and salts thereof; 2-phosphonobutane-1,2,4-tricarboxylic acid and salts thereof; and any combination thereof.

The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

The laundry detergent composition may comprise one or more polymers. Suitable polymers include carboxylate polymers, polyethylene glycol polymers, polyester soil release polymers such as terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, and any combination thereof.

Other suitable cellulosic polymers may have a degree of substitution (DS) of from 0.01 to 0.99 and a degree of blockiness (DB) such that either DS+DB is of at least 1.00 or DB+2DS-DS' is at least 1.20. The substituted cellulosic polymer can have a degree of substitution (DS) of at least 0.55. The substituted cellulosic polymer can have a degree of blockiness (DB) of at least 0.35. The substituted cellulosic polymer can have a DS+DB, of from 1.05 to 2.00. A suitable substituted cellulosic polymer is carboxymethylcellulose.

Another suitable cellulosic polymer is cationically modified hydroxyethyl cellulose.

Suitable perfumes include perfume microcapsules, polymer assisted perfume delivery systems including Schiff base perfume/polymer complexes, starch-encapsulated perfume accords, perfume-loaded zeolites, blooming perfume accords, and any combination thereof. A suitable perfume microcapsule is melamine formaldehyde based, typically comprising perfume that is encapsulated by a shell comprising melamine formaldehyde. It may be highly suitable for such perfume microcapsules to comprise cationic and/or cationic precursor material in the shell, such as polyvinyl formamide (PVF) and/or cationically modified hydroxyethyl cellulose (catHEC).

Suitable suds suppressors include silicone and/or fatty acid such as stearic acid.

The laundry detergent composition maybe coloured. The colour of the liquid laundry detergent composition may be the same or different to any printed area on the film of the article. Each compartment of the unit dose article may have a different colour. Preferably, the liquid laundry detergent composition comprises a non-substantive dye having an average degree of alkoxylation of at least 16.

Other Compositions

The composition for use inside the unit dose article may be a non-detergent composition and/or a non-household care composition. A fabric or household care composition includes fabric treatments, hard surfaces, air care, car care, dishwashing, fabric conditioning and softening, laundry detergency, laundry and rinse additive and/or care, hard surface cleaning and/or treatment, and other cleaning for consumer or institutional use. Non-household care compositions are for other uses. For example, a non-household care composition can be selected from agricultural compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, including cleaning and detergent compositions applicable to any such use while excluding fabric and household care compositions.

It is contemplated that one type of embodiment will include an article as described herein with a sealed compartment containing a fabric care or household care composition, a film including a blend of a polyvinyl alcohol homopolymer and an anionic polyvinyl alcohol copolymer, and both the first water soluble film and the second water soluble film include blends include 65 wt. % or greater of an anionic polyvinyl alcohol copolymer.

It is contemplated that another type of embodiment will include an article as described herein with a sealed compartment containing a fabric care or household care composition, a film including a blend of at least two anionic polyvinyl alcohol copolymers, and both then first water soluble film and the second water soluble film include blends of at least two anionic polyvinyl alcohol copolymers.

In one type of embodiment, the composition can include an agrochemical, e.g. one or more insecticides, fungicides, herbicides, pesticides, miticides, repellants, attractants, defoliaments, plant growth regulators, fertilizers, bactericides, micronutrients, and trace elements. Suitable agrochemicals and secondary agents are described in U.S. Pat. Nos. 6,204,223 and 4,681,228 and EP 0989803 A1. For example, suitable herbicides include paraquat salts (for example paraquat dichloride or paraquat bis(methylsulphate), diquat salts (for example diquat dibromide or diquat alginate), and glyphosate or a salt or ester thereof (such as glyphosate isopropylammonium, glyphosate sesquisodium or glyphosate trimesium, also known as sulfosate). Incompatible pairs of crop protection chemicals can be used in separate chambers, for example as described in U.S. Pat. No. 5,558,228. Incompatible pairs of crop protection chemicals that can be used include, for example, bensulfuron methyl and molinate; 2,4-D and thifensulfuron methyl; 2,4-D and methyl 2-[[[[N-4-methoxy-6-methyl-1,3,5-triazine-2-yl)-N-methylamino]carbonyl]amino]-sulfonyl]benzoate; 2,4-D and metsulfuron methyl; maneb or mancozeb and benomyl; glyphosate and metsulfuron methyl; tralomethrin and any organophosphate such as monocrotophos or dimethoate; bromoxynil and N-[[4,6-dimethoxypyrimidine-2-yl)-amino]carbonyl]-3-(ethylsulfonyl)-2-pyridine-sulfonamide; bromoxynil and methyl 2-[[[[(4-methyl-6-methoxy)-1,3,5-triazin-2-yl)amino]carbonyl]amino]sulfonyl]-benzoate; bromoxynil and methyl 2-[[[[N-(4-methoxy-6-methyl-1,3,5-triazin-2-yl)-N-methylamino]carbonyl]amino]-sulfonyl] benzoate. In another, related, type of embodiment, the composition can include one or more seeds, optionally together with soil, and further optionally together with one or more additional components selected from mulch, sand, peat moss, water jelly crystals, and fertilizers, e.g. including types of embodiments described in U.S. Pat. No. 8,333,033.

In another type of embodiment, the composition is a water-treatment agent. Such agents include aggressive oxidizing chemicals, e.g. as described in U.S. Patent Application Publication No. 2014/0110301 and U.S. Pat. No. 8,728,593. For example, sanitizing agents can include hypochlorite salts such as sodium hypochlorite, calcium hypochlorite, and lithium hypochlorite; chlorinated isocyanurates such as dichloroisocyanuric acid (also referred to as "dichlor" or dichloro-s-triazinetrione, 1,3-dichloro-1,3,5-triazinane-2,4,6-trione) and trichloroisocyanuric acid (also referred to as "trichlor" or 1,3,5-trichloro-1,3,5-triazinane-2,4,6-trione). Salts and hydrates of the sanitizing compounds are also contemplated. For example, dichloroisocyanuric acid may be provided as sodium dichloroisocyanurate, sodium dichloroisocyanurate acid dihydrate, among others. Bromine containing sanitizing agents may also be suitable for use in unit dose packaging applications, such as 1,3-dibromo-5,5-dimethylhydantoin (DBDMH), 2,2-dibromo-3-nitrilopropionamide (DBNPA), dibromocyano acetic acid amide, 1-bromo-3-chloro-5,5-dimethylhydantoin; and 2-bromo-2-nitro-1,3-propanediol, among others. The oxidizing agent can be one described in U.S. Pat. No. 7,476,325, e.g. potassium hydrogen peroxymonosulfate. The composition can be a pH-adjusting chemical, e.g. as described in U.S. Patent Application Publication No. 2008/0185347, and can include, for example, an acidic component and an alkaline component such that the composition is effervescent when contacted with water, and adjusts the water pH. Suitable ingredients include sodium bicarbonate, sodium bisulfate, potassium hydroxide, sulfamic acid, organic carboxylic acids, sulfonic acids, and potassium dihydrogen phosphate. A buffer blend can include boric acid, sodium carbonate, glycolic acid, and oxone monopersulfate, for example.

A water-treatment agent can be or can include a flocculant, e.g. as described in U.S. Patent Application Publication No. 2014/0124454. The flocculant can include a polymer flocculant, e.g. polyacrylamide, a polyacrylamide copolymer such as an acrylamide copolymers of diallydimethylammonium chloride (DADMAC), dimethylaminoethylacrylate (DMAEA), dimethylaminoethylmethacrylate (DMAEM), 3-methylamidepropyltrimethylammonium chloride (MAPTAC) or acrylic acid; a cationic polyacrylamide; an anionic polyacrylamide; a neutral polyacrylamide; a polyamine; polyvinyl amine; polyethylene imine; polydimethyldiallylammonium chloride; poly oxyethylene; polyvinyl alcohol; polyvinyl pyrrolidone; polyacrylic acid; polyphosphoric acid; polystyrene sulfonic acid; or any combination thereof. A flocculant can be selected from chitosan acetate, chitosan lactate, chitosan adipate, chitosan glutamate, chitosan succinate, chitosan malate, chitosan citrate, chitosan fumarate, chitosan hydrochloride, and combinations thereof. The water-treating composition can include a phosphate removing substance, e.g. one or more selected from a zirconium compound, a rare earth lanthanide salt, an aluminum compound, an iron compound, or any combination thereof.

The composition can be a limescale removing composition, e.g. citric or maleic acid or a sulphate salt thereof, or any mixture thereof, e.g. as described in U.S. Patent Application No. 2006/0172910. Various other types of compositions are contemplated for use in the unit dose articles described herein, including particulates, for example down feathers, e.g. as described in U.S. RE29059 E; super absorbent polymers, e.g. as described in U.S. Patent Application Publication Nos. 2004/0144682 and 2006/0173430; pigments and tinters, e.g. as described in U.S. Pat. No. 3,580,390 and U.S. Patent Application Publication No. 2011/0054111; brazing flux (e.g. alkali metal fluoroaluminates, alkali metal fluorosilicates and alkali metal fluorozincates), e.g. as described in U.S. Pat. No. 8,163,104; food items (e.g., coffee powder or dried soup) as described in U.S. Patent Application Publication No. 2007/0003719; and wound dressings, e.g. as described in U.S. Pat. No. 4,466,431.

At least one compartment of the unit dose article may comprise a solid. If present, the solid may be present at a concentration of at least 5% by weight of the unit dose article.

Method of Making a Unit Dose Article

Those skilled in the art will be aware of processes to make the detergent or other composition of the present invention. Those skilled in the art will be aware of standard processes and equipment to make the detergent or other compositions.

Those skilled in the art will be aware of standard techniques to make the unit dose article according to any aspect of the present invention. Standard forming processes including but not limited to thermoforming and vacuum forming techniques may be used.

A preferred method of making the water-soluble unit dose article according to the present invention comprises the steps of moulding the first water-soluble film in a mould to form an open cavity, filling the cavity with the detergent or orther composition, laying the second film over the first film to close the cavity, and sealing the first and second films together preferably through solvent sealing, the solvent preferably comprising water, to produce the water-soluble unit dose article.

Test Protocols

Unit Dose Article Machine Wash Dissolution Test Method

This method is designed to assess the relative dissolution properties of laundry water soluble unit dose articles under stressed washing machine conditions. For this method Electrolux Programmable Washing machines type W565H, an adjusted EMPA221 load (EMPA221 source: Swissatest—SWISSatest testsmaterials, Movenstrasse 12 CH9015 St Gallen, Switzerland) and Digieye picture taking equipment (Digieye by VeriVide) were used.

The adjusted EMPA221 load was prepared by coloring the load into an orange color by using commercially available dying solutions for in washing machines dying (Dylon goldfish orange washing machine dye (No 55)). To color the load any standard household washing machine can be used, employing a standard cotton cycle at 40° C. 500 g of salt and 200 g of the Dylon goldfish orange machine dye are added to the drum of the washing machine. The drum was consequently moved to the left and the right until the salt and the dye were not visible anymore. 25 EMPA 221 items (size of 50 cm×50 cm, overlocked on the edges to prevent fraying), were consequently evenly distributed over the drum without folding of the items. A standard cotton cycle at 40° C. was run at a water hardness of 15 gpg. After completion of the cycle 50 g of Ariel Sensitive powder was added into the dispenser and a normal cotton cycle at 40° C. was run at a water hardness of 15 gpg. After completion of this cycle 2 additional normal cotton cycles at 40° C. without any detergent were run at a water hardness of 15 gpg, followed by line-drying the items.

To note: Brand new EMPA221 items must be desized before coloring them by adding 25 items into a front loading Miele washing machine and running 2 short cotton cycles at 60° C. (approximate duration of 1 h 30) with 50 g of Ariel sensitive powder and a water hardness of 15 gpg, followed by running 2 more short cotton cycles at 60° C. (approximate duration of 1 h 30) with no detergent and a water hardness of 15 gpg, followed by tumble drying.

The Electrolux W565 programmable washing machines were programmed with 2 programs. The first program was designed to equally wet the load (pre-wet program). The second program (dissolution program) was utilized to simulate 10 min of a Western Europe stressed cycle setting, followed by pumping out the water and starting a spin of 3 min at 1100 rpm.

|  |  | Pre-wet program | Dissolution program |
|---|---|---|---|
| Wash | Time | 5 min | 10 min |
|  | Motor rotation | 49 rpm | 40 rpm |
|  | Water intake | 12 L | 4 L |
|  | Heating | No heating | No heating |
|  | Motor action time clockwise | 28 s | 28 s |
|  | Motor resting time | 12 s | 12 s |
|  | Motor action time Counterclockwise | 28 s | 28 s |
| Drain | Draining time | 20 s | 20 s |
|  | Motor rotation | 20 rpm | 49 rpm |
| Extraction | Time | NA | 3 min |
|  | Motor rotation | NA | 1100 rpm |

A load consisting of 50 dyed EMPA221 fabrics (ca. 2.45 kg) was evenly introduced in the Electrolux W565 washing machine and the pre-wet program was started. After the pre-wet program, 6 water soluble unit dose articles were distributed evenly across the wet load, after which the dissolution program was initiated. At the end of the full program, the wet load was transferred to a grading room (equipped with D65 lighting conditions) to be assessed for residues by expert graders. Each fabric which had discoloration spots due to remnant detergent or excess polymer resin, was selected out of the load for image analysis.

This image analysis was conducted by acquiring pictures of each side of the selected fabrics using the Digi-Eye camera (setting: "d90 Diffuse Light. Shutter time ¼. Aperture 8"). The fabrics should be put onto a gray or black background to enhance the contrast. After this the image was assessed through image analysis software to calculate the total size of residue detected in the load (pixel count). This tool detects residues by identifying spots that are of a different color than the normal ballast, using delta E thresholding (delta E of 6). For one machine and load a residue score is then calculated by summing the total area of residues present in the load. The logarithmic value of the total residue area is calculated and the average of 4 external replicates, i.e. 4 different washing machine runs, was reported.

Unit Dose Article Strength and Seal Failure Test Method

This test method describes the practice for determining the unit dose article strength and seal failure using the Instron Universal Materials Testing instrument (Instron Industrial Products, 825 University Ave., Norwood, Mass. 02062-2643) with a load cell of maximum 100 kN (kilo Newton). Via compression of a unit dose article, this method determines the overall strength (in Newtons) of the unit dose article by putting pressure on the film and seal regions. Unit dose article strength (in Newtons) is defined as the maximum load a unit dose article can support before it breaks. Unit dose articles opening at the seal area at a pressure lower than 250N are reported as seal failures, and are not taken into account when determining average unit dose article strength.

The unit dose article strength and seal failure is measured no sooner than one hour after unit dose article production so that the film/unit dose articles had time to set after converting. The method was performed in a room environment between 30-40% relative humidity (RH) and 20-23° C. Stored unit dose articles were allowed to re-equilibrate to the testing room environment for one hour prior to testing.

FIG. 1. shows a schematic illustration of the basic configuration of the unit dose article strength test and seal failure test. To measure unit dose article strength and seal failure, a unit dose article 510 was enclosed in a plastic de-aerated bag 500 (150 mm by 124 mm with closure, 60 micron thick—e.g. Raja grip RGP6B) to prevent contamination of working environment upon unit dose article rupture. After enclosure in the bag, the unit dose article 510 is centered between two compression plates 520, 530 of the instrument. The unit dose article 510 is placed in an upright position, so that the width seal dimension 540 (e.g. smallest dimension within a defined rectangular plane just encompassing the seal area, 41 mm in actual unit dose articles tested) is between the compression plates (x-direction) such that the stress is applied on the width seal. For the compression, the speed of decreasing the distance between the plates 520 and 530 is set at 60 mm/min. Ten replicates are conducted per test leg, and average unit dose article strength and seal failure data are reported.

Tensile Strain Test and e-Modulus Test

A water-soluble film characterized by or to be tested for tensile strain according to the Tensile Strain (TS) Test and e-modulus (elongation modulus or tensile stress) according to the Modulus (MOD) Test was analyzed as follows. The procedure includes the determination of tensile strain and the determination of e-modulus according to ASTM D 882 ("Standard Test Method for Tensile Properties of Thin Plastic Sheeting"). An INSTRON tensile testing apparatus (Model 5544 Tensile Tester or equivalent—Instron Industrial Products, 825 University Ave., Norwood, Mass. 02062-2643) was used for the collection of film data. A minimum of three test specimens, each cut with reliable cutting tools (e.g. JDC precision sample cutter, Model 1-10, from Thwing Albert Instrument Company, Philadelphia, Pa. U.S.A.) to ensure dimensional stability and reproducibility, were tested in the machine direction (MD) (where applicable), i.e. water soluble film roll winding/unwinding direction, for each measurement. Water soluble films were pre-conditioned to testing environmental conditions for a minimum of 48 h. Tests were conducted in the standard laboratory atmosphere of 23±2.0° C. and 35±5% relative humidity. For tensile strain or modulus determination, 1"-wide (2.54 cm) samples of a single film sheet having a thickness of 3.0±0.15 mil (or 76.2±3.8 µm) are prepared. For e-modulus testing virgin films were tested. For tensile strain testing test films were first pre-immersed in testing detergent according to the protocol described below. The sample was then transferred to the INSTRON tensile testing machine to proceed with testing. The tensile testing machine was prepared according to manufacturer instructions, equipped with a 500 N load cell, and calibrated. The correct grips and faces were fitted (INSTRON grips having model number 2702-032 faces, which are rubber coated and 25 mm wide, or equivalent). The samples were mounted into the tensile testing machine, elongated at a rate of 1N/min, and analyzed to determine the e-modulus (i.e., slope of the stress-strain curve in the elastic deformation region) and tensile strain at break (i.e., % elongation achieved at the film break, i.e. 100% reflects starting length, 200% reflects a film that has been lengthened 2 times at film break). The average of minimum three test specimens was calculated and reported.

Film Pre-Immersion Protocol

A film sample measuring 11 cm by 12 cm was prepared of both films intended to be used to form a sealed compartment enclosing a liquid household detergent composition. A total of 750 ml of the household liquid detergent composition intended to be enclosed within a sealed compartment comprising the test films, was required for each test film. The bottom of a clean inert glass recipient was covered with a thin layer of liquid and the film to be tested was spread on the liquid; air bubbles trapped under the film were gently pushed towards the sides. The remaining liquid was then gently poured on top of the film, in such a way that the film was fully immersed into the liquid. The film should remain free of wrinkles and no air bubbles should be in contact with the film. The film stayed in contact with the liquid and was stored under closed vessel conditions for 6 days at 35° C. and 1 night at 21° C. A separate glass recipient was used for each test film. The film was then removed from the storage vessel, and the excess liquid was removed from the film. A piece of paper was put on the film which was laid on top of a bench paper, and then the film was wiped dry thoroughly with dry paper. Films were consequently pre-conditioned to tensile strain environmental testing conditions as described above. When intending enclosing solid household detergent compositions, virgin films were used for tensile strain testing.

Method for Measurement of Water Capacity

Water capacity was measured with a DVS (Dynamic Vapor Sorption) Instrument. The instrument used was a SPS-DVS (model SPSx-1µ-High load with permeability kit) from ProUmid. The DVS uses gravimetry for determination of moisture sorption/desorption and is fully automated.

The accuracy of the system is ±0.6% for the RH (relative humidity) over a range of 0-98% and ±0.3° C. at a temperature of 25° C. The temperature can range from +5 to +60° C. The microbalance in the instrument is capable of resolving 0.1 µg in mass change. 2 replicates of each film are measured and the average water capacity value is reported.

For the specific conditions of the test, a 6 pan carousel which allows to test 5 films simultaneously (1 pan is used as a reference for the microbalance and needs to remain empty) was used.

Each pan has an aluminum ring with screws, designed to fix the films. A piece of film was placed onto a pan and after gentle stretching, the ring was placed on top and the film was tightly fixed with the screws and excess film removed. The film covering the pan surface had an 80 mm diameter.

The temperature was fixed at 20° C. Relative humidity (RH) was set at 35% for 6 hours, and then gradually raised onto 50% in 5 min. The RH remained at 50% for 12 hours. The total duration of the measurement was 18 hours.

The cycle time (=time between measuring each pan) was set to 10 min and the DVS records each weight result vs. time and calculates automatically the % Dm (relative mass variation versus starting weight of the film, i.e. 10% reflects a 10% film weight increase versus starting film weight).

The water capacity (or % Dm gained over 50% RH cycle during the fixed time of 12 hours at 20° C.) was calculated by difference of the value % Dm at 50% RH (last value measured at 50% RH) minus % Dm at 35% RH (last value before going up to 50% RH).

Dissolution and Disintegration Test (MSTM 205)

A film can be characterized by or tested for Dissolution Time and Disintegration Time according to the MonoSol Test Method 205 (MSTM 205), a method known in the art and discussed in US20160024446.

The following embodiments are also contemplated:

1. A water soluble pouch comprising at least one sealed compartment optionally comprising at least one composition, the pouch comprising a first water soluble film and a second water soluble film;

wherein the first water soluble film is sealed to the second water soluble film to form the at least one sealed compartment;

wherein the first water soluble film has a first water capacity and a first tensile strain at break;

wherein the second water soluble film has a second water capacity and a second tensile strain at break;

wherein the first water capacity is less than the second water capacity and the difference between the first water capacity and the second water capacity is from about 0.01 to about 1, or from about 0.03 to about 0.5 or from about 0.05 to about 0.3 wherein the first tensile strain at break is greater than the second tensile strain at break and the difference between the first tensile strain at break and the second tensile strain at break is from about 10 to about 1000 or from about 100 to about 750 or from about 200 to about 500/

2. The water soluble pouch of embodiment 1, wherein the first water soluble film has a first elongation modulus, the second water soluble film has a second elongation modulus, the first elongation modulus is greater than the second elongation modulus, and the difference between the first elongation modulus and the second elongation modulus is from about 0.5 mPa to about 10 mPa, or from about 1 mPa to about 8 mPa, or from about 2 mPa to about 7 mPa.

3. The water soluble pouch according to any one of the preceding embodiments, wherein the first water capacity is from about 4 to about 6.

4. The water soluble pouch according to any one of the preceding embodiments, wherein the second water capacity is from about 4 to about 6

5. The water soluble pouch according to any one of the preceding embodiments, wherein the first tensile strain at break is from about 500 to about 1200, or about 700 to about 1200, or about 900 to about 1200.

6. The water soluble pouch according to any one of the preceding embodiments, wherein the second tensile strain at break is from about 500 to about 1200, or about 500 to about 1000, or about 500 to about 900.

7. The water soluble pouch of embodiment 2, wherein the first elongation modulus is from about 8 to about 20, or from about 10 to about 20.

8. The water soluble pouch of embodiment 2, wherein the second elongation modulus is from about 8 to about 20, or from about 8 to about 15.

9. The water soluble pouch according to any one of the preceding embodiments, wherein the first water soluble film is thermoformed prior to incorporation into the pouch.

10. The water soluble pouch according to any one of the preceding embodiments, wherein the second water soluble film is not thermoformed prior to incorporation into the pouch.

11. The water soluble pouch according to any one of the preceding embodiments, wherein the first water soluble film and the second water soluble film each has a thickness of about 76 microns and dissolution time prior to incorporation into the pouch of about 300 seconds or less in water at a temperature of 20° C. in accordance with MonoSol Test Method MSTM-205.

12. The water soluble pouch according to any one of the preceding embodiments, wherein the pouch has a pouch strain of at least about 200 N as measured by the first water soluble film sealed, conditioned, and tested according to the Pouch Strain Test.

13. The water soluble pouch according to any one of the preceding embodiments, wherein the second water soluble film has a tackiness value prior to incorporation into the pouch of at least about 1500 in accordance with the Tackiness PA Test 14. The water soluble pouch according to any one of the preceding embodiments, wherein the first water soluble film comprises a first water soluble resin and the second water soluble film comprises a second water soluble resin.

15. The water soluble pouch of embodiment 14, wherein the first water soluble resin comprises a polyvinyl alcohol or copolymer thereof and the second water soluble resin comprises a polyvinyl alcohol or a copolymer thereof.

16. The water soluble pouch of embodiment 14, wherein the first water soluble resin comprises a blend of a polyvinyl alcohol homopolymer and a polyvinyl alcohol copolymer comprising an anionic monomer unit.

17. The water soluble pouch of embodiment 16, wherein the blend comprises from about 30 to about 100 weight percent of the polyvinyl alcohol copolymer comprising an anionic monomer unit and from about 0 to about 70 weight percent of the polyvinyl alcohol homopolymer, based on the total weight of polyvinyl alcohol in the film.

18. The water soluble pouch of embodiment 17, wherein the blend comprises from about 30 to about 70 weight percent, or from about 30 to about 65 weight percent, or from about 30 to about 50 weight percent of the polyvinyl alcohol copolymer comprising an anionic monomer unit, based on the total weight of polyvinyl alcohol in the film.

19. The water soluble pouch of embodiment 14, wherein the second water soluble resin comprises a blend of a polyvinyl alcohol homopolymer and a polyvinyl alcohol copolymer comprising an anionic monomer unit.

20. The water soluble pouch of embodiment 19, wherein the blend comprises from about 30 to about 100 weight percent of the polyvinyl alcohol copolymer comprising an anionic monomer unit and from about 0 to about 70 weight percent of the polyvinyl alcohol homopolymer, based on the total weight of polyvinyl alcohol in the film.

21. The water soluble pouch of embodiment 20, wherein the blend comprises from about 30 to about 70 weight percent, or from about 30 to about 65 weight percent, or from about 30 to about 50 weight percent of the polyvinyl alcohol copolymer comprising an anionic monomer unit, based on the total weight of polyvinyl alcohol in the film.

22. The water soluble pouch of any one of embodiments 16 to 21, wherein the anionic monomer unit is selected from the group consisting of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methyl acrylamido-2-methylpropanesulfonic acid, 2-sulfoethyl acrylate, alkali metal salts thereof, esters thereof, and combinations thereof.

23. The water soluble pouch of embodiment 22, wherein the anionic monomer unit is selected from the group consisting of maleic acid, monoalkyl maleate, dialkyl maleate, maleic anhydride, alkali metal salts thereof, esters thereof, and combinations thereof.

24. The water soluble pouch of embodiment 23, wherein the anionic monomer unit is selected from the group consisting of maleic acid, monomethyl maleate, dimethyl maleate, maleic anyhydride, alkali metal salts thereof, esters thereof, and combinations thereof.

25. The water soluble pouch of any one of embodiments 16 to 24, wherein the polyvinyl alcohol copolymer comprises from about 2 mol % to about 8 mol % of the anionic monomer unit, or from about 1 mol % to about 4 mol % of the anionic monomer unit.

26. The water soluble pouch according to any one of the preceding embodiments, wherein the first water soluble resin comprises polyvinyl alcohol having a degree of hydrolysis in a range of about 87 to about 93.

27. The water soluble pouch according to any one of the preceding embodiments, wherein the first water soluble resin comprises a blend of a polyvinyl alcohol homopolymer and a polyvinyl alcohol copolymer comprising an anionic monomer unit, wherein the blend has an arithmetic weight average degree of hydrolysis in the range of about 87 to about 93.

28. The water soluble pouch according to any one of the preceding embodiments, wherein the pouch has a pouch strain of less than 2000 N as measured by the first water soluble film sealed, conditioned, and tested according to the Burst Strength Test.

29. The water soluble pouch according to any one of the preceding embodiments, wherein the first water soluble film further comprises a plasticizer.

30. The water soluble pouch according to any one of the preceding embodiments, wherein the second water soluble film further comprises a plasticizer.

31. The water soluble pouch of embodiment 31 or embodiment 32, wherein the plasticizer is selected from the group consisting of glycerine, trimethylol propane, sorbitol, and combinations thereof.

32. The water soluble pouch according to any one of the preceding embodiments, wherein the first water soluble film further comprises a surfactant.

33. The water soluble pouch according to any one of the preceding embodiments, wherein the second water soluble film further comprises a surfactant.

34. The water soluble pouch of embodiment 34 or embodiment 35, wherein the surfactant is selected from the group consisting of polyoxyethylenated polyoxypropylene glycols, alcohol ethoxylates, alkylphenol ethoxylates, tertiary acetylenic glycols, alkanolamides, polyoxyethylenated amines, quaternary ammonium salts, quaternized polyoxyethylenated amines, amine oxides, N-alkylbetaines, sulfobetaines, and mixtures thereof.

35. The water soluble pouch according to any one of the preceding embodiments, wherein the first water soluble film further comprises an aversive agent.

36. The water soluble pouch according to any one of the preceding embodiments, wherein the second water soluble film further comprises an aversive agent.

37. The water soluble pouch according to any one of the preceding embodiments, wherein the thickness of the first water soluble film does not vary from the thickness of the second water soluble film by more than 10%.

38. The water soluble pouch according to embodiment 14, wherein the first water soluble resin has a 4% solution viscosity at 25° C. in a range of about 12 cP to about 40 cP, or about 12 cP to about 30 cP, or about 14 cP to about 25 cP.

39. The water soluble pouch according to embodiment 14, wherein the second water soluble resin has a 4% solution viscosity at 25° C. in a range of about 4 cP to about 35 cP, or about 10 cP to about 20 cP, or about 10 cP to about 15 cP, or about 12 cP to about 14 cP.

40. The water soluble pouch according to embodiment 14, wherein the 4% solution viscosity at 25° C. of the first water soluble resin is greater than the 4% solution viscosity at 25° C. of the second water soluble resin and the difference between the 4% solution viscosity at 25° C. of the first water soluble resin and the 4% solution viscosity at 25° C. of the second water soluble resin is about 2 cP about 20 cP, or about 3 cP to about 15 cP, or about 4 cP to about 12 cP.

41. The water soluble pouch according to any one of the preceding embodiments, wherein the composition in the sealed compartment is a non-household care composition.

EXAMPLES

The following unit dose articles are prepared and tested for unit dose article strength, seal failure, and pouch dissolution per the protocols described herein. Comparative unit dose article(s) outside the scope of the invention are prepared out of a single film type while example unit dose articles according to the invention are prepared out of two different films, differing in molecular weight of the homopolymer.

Multi-compartment water soluble unit dose articles with a 41 mm×43 mm footprint, cavity depth of 20.1 mm and cavity volume of 25 ml, are made through thermo/vacuum forming. For dual film example unit dose article film A is deformed under vacuum while film B is used as a closing film. A standard detergent composition, as commercially available in the UK in January 2016 in the bottom compartment of Fairy non-Bio 3-in-1 water soluble unit dose article product was enclosed inside these single compartment unit dose articles.

Table 1 below details film compositions used to prepare unit dose articles.

TABLE 1

|  | Resin content in film | Blend ratio | Polymer 1 (anionic-PVOH copolymer) | | | | Polymer 2 (PVOH homopolymer) | |
| --- | --- | --- | --- | --- | --- | --- | --- | --- |
|  |  |  | Anionic source | Anionic substitution | dH | 4% viscosity | dH | 4% viscosity |
| Case 1 | | | | | | | | |
| Film A | 65% | 30/70 | Monomethyl maleate (carboxylated) | 4% | 89% | 16 cps | 88% | 18 cps |
| Film B | 65% | 50/50 | Monomethyl maleate (carboxylated) | 4% | 89% | 16 cps | 88% | 18 cps |

TABLE 1-continued

| | Resin content in film | Blend ratio | Polymer 1 (anionic-PVOH copolymer) | | | | Polymer 2 (PVOH homopolymer) | |
| --- | --- | --- | --- | --- | --- | --- | --- | --- |
| | | | Anionic source | Anionic substition | dH | 4% viscosity | dH | 4% viscosity |
| Film C | 65% | 70/30 | Monomethyl maleate (carboxylated) | 4% | 89% | 16 cps | 88% | 18 cps |

Unit dose articles, e.g., pouches, made from films having increased anionic content exhibit increased stickiness. By combining films that are chemically different from each other, with respect to the anionic content of the films, a water-soluble unit dose article exhibiting optimal dissolution and reduced stickiness may be obtained.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-soluble unit dose article comprising at least one sealed compartment optionally comprising at least one composition contained in the article, the water-soluble unit dose article comprising a first water soluble film comprising a PVOH polymer comprising a first anionic content;
    and a second water soluble film comprising a PVOH polymer comprising a second anionic content;
    wherein the first anionic content is in a range of about 0.5 mol % to about 10 mol % of total PVOH polymer in the first water soluble film and the second anionic content is in a range of about 0 mol % to about 5 mol % of total PVOH polymer in the second water soluble film, and the difference between the first anionic content and second anionic content is about 0.05 mol % to about 4 mol %, wherein the anionic content of each film is the molar percentage of anionic monomer units present in the total PVOH polymer of the film, and wherein the first water-soluble film is chemically different from the second water soluble film with respect to the anionic content of the PVOH polymers of the films;
    wherein the first film is sealed to the second film to form the at least one sealed compartment;
    wherein the first water soluble film comprises a first water soluble PVOH resin and the second water soluble film comprises a second water soluble PVOH resin;
    wherein the first water soluble resin comprises a first blend of at least one polyvinyl alcohol copolymer comprising an anionic monomer unit(s) and at least one polyvinyl alcohol homopolymer, the second water soluble resin comprises a second blend of at least one polyvinyl alcohol copolymer comprising an anionic monomer unit(s) and at least one polyvinyl alcohol homopolymer, and the first blend is chemically different from the second blend; and
    wherein the first blend comprises a monomethyl maleate modified PVOH resin and a PVOH homopolymer resin and the second blend comprises a monomethyl maleate modified PVOH resin and a PVOH homopolymer resin;
    provided that when the composition is a fabric care or household care composition and a film comprises a blend of a polyvinyl alcohol homopolymer resin and an anionic polyvinyl alcohol copolymer resin, then both the first water soluble film and the second water soluble film comprise blends that include 65 wt. % or greater of an anionic polyvinyl alcohol copolymer resin, based on the total weight of polyvinyl alcohol resins in the blend; and
    provided that when the composition is a fabric care or household care composition and a film comprises a blend of at least two anionic polyvinyl alcohol copolymer resins, then both then first water soluble film and the second water soluble film comprise blends of at least two anionic polyvinyl alcohol copolymer resins.

2. The water-soluble unit dose article of claim 1, wherein the first anionic content is greater than the second anionic content.

3. The water-soluble unit dose article according to claim 1, wherein the first water soluble resin comprises a first blend of two or more polyvinyl alcohol copolymers comprising anionic monomer unit(s), the second water soluble resin comprises a second blend of two or more polyvinyl alcohol copolymers comprising anionic monomer unit(s), and the first blend is chemically different from the second blend.

4. The water-soluble unit dose article of claim 1, wherein the first water soluble resin comprises from 65% by weight or greater of the first water soluble resin of the polyvinyl alcohol copolymer comprising an anionic monomer unit and the second water soluble resin comprises from 65% by weight or greater of the second water soluble resin of the polyvinyl alcohol copolymer comprising an anionic monomer unit.

5. The water-soluble unit dose article of claim 1, wherein the first water soluble resin comprises from about 1% to about 70% by weight of the first water soluble resin of the polyvinyl alcohol copolymer comprising an anionic monomer unit and from about 30% to about 99% by weight of the first water soluble resin of the polyvinyl alcohol homopolymer.

6. The water-soluble unit dose article of claim 5, wherein the first water soluble resin comprises from about 10 wt % to about 70 wt % by weight of the first water soluble resin of the polyvinyl alcohol copolymer comprising an anionic monomer unit.

7. The water-soluble unit dose article of claim 1, wherein the second water soluble resin comprises from about 1 wt % to about 70 wt % by weight of the second water soluble resin of the polyvinyl alcohol copolymer comprising an anionic monomer unit and from about 30 wt % to about 99 wt % by weight of the second water soluble resin of the polyvinyl alcohol homopolymer.

8. The water-soluble unit dose article of claim 7, wherein the second water soluble resin comprises from about 10 wt % to about 70 wt % by weight of the second water soluble resin of the polyvinyl alcohol copolymer comprising an anionic monomer unit.

9. The water-soluble unit dose article of claim 1, wherein the first water soluble resin comprises from about 10 wt % to about 32 wt % by weight of the first water soluble resin of the polyvinyl alcohol copolymer comprising an anionic monomer unit and the second water soluble resin comprises from about 33 wt % to about 50 wt % by weight of the second water soluble resin of the polyvinyl alcohol copolymer comprising an anionic monomer unit.

10. The water-soluble unit dose article of claim 1, wherein the first water soluble resin comprises at least one polyvinyl alcohol copolymer(s) comprising from about 2 mol % to about 8 mol % of the anionic monomer unit with respect to total polyvinyl alcohol copolymer present.

11. The water-soluble unit dose article of claim 1, wherein the second water soluble resin comprises at least one polyvinyl alcohol copolymer(s) comprising from about 2 mol % to about 8 mol % of the anionic monomer unit with respect to total polyvinyl alcohol copolymer present.

12. The water-soluble unit dose article of claim 1, wherein the first water soluble resin comprises at least one polyvinyl alcohol copolymer(s) comprising from about 1 mol % to about 3 mol % of the anionic monomer unit with respect to total polyvinyl alcohol copolymer present and the second water soluble resin comprises at least one polyvinyl alcohol copolymer(s) comprising from about 4 mol % to about 8 mol % of the anionic monomer unit with respect to total polyvinyl alcohol copolymer present.

13. The water-soluble unit dose article according to claim 1, wherein the first water soluble film is a thermoformed film.

14. The water-soluble unit dose article according to claim 13, wherein the second water soluble film is not a thermoformed film.

15. The water-soluble unit dose article according to claim 1, wherein the anionic content of the a first water soluble film or the a second water soluble film further comprises an anionic monomer unit derived from a monomer selected from the group consisting of vinyl acetic acid, alkyl acrylates, maleic acid, monoalkyl maleate other than monomethyl maleate, dialkyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts thereof, esters thereof, and combinations thereof.

16. The water-soluble unit dose article of claim 1, wherein the PVOH resin of the first water soluble film comprises a first anionic content, the PVOH resin of the second water soluble film comprises a second anionic content, and the first anionic content is greater than the second anionic content.

17. The water-soluble unit dose article according to claim 1, wherein the water-soluble unit dose article is a pouch and has a pouch strength of less than about 2000 N in accordance with the Pouch Strength Test.

18. The water-soluble unit dose article according to claim 1, wherein the first water-soluble film and the second water-soluble film each independently comprises from about 30 wt % to about 90 wt % by weight of the film of water-soluble resin.

19. The water-soluble unit dose article according to claim 1, wherein the first water-soluble film and the second water-soluble film each independently has a thickness prior to incorporation into the water-soluble unit dose article of about 40 microns to about 100 microns.

20. The water-soluble unit dose article according to claim 1, wherein the first water-soluble film and the second water-soluble film each independently has a dissolution time prior to incorporation into the water-soluble unit dose article of about 300 seconds or less in water at a temperature of 20° C. for a film having a thickness of about 76 micron in accordance with MonoSol Test Method MSTM-205.

21. The water-soluble unit dose article according to claim 1, wherein the water-soluble unit dose article has an average Log(residue area) of less than about 6.2 per the unit dose article machine wash dissolution test method.

22. The water-soluble unit dose article according to claim 1, wherein the thickness of the first water soluble film does not vary from the thickness of the second water soluble film by more than 10%.

23. The water-soluble unit dose article according to claim 1, wherein the thickness of the first water-soluble film is the same as the thickness of the second water-soluble film.

24. The water-soluble unit dose article according to claim 1, wherein the water-soluble unit dose article is a pouch and has a pouch strength of at least about 350N in accordance with the Pouch Strength Test.

25. The water-soluble unit dose article according to claim 1, wherein the water-soluble unit dose article has 0 seal failures in accordance with the Seal Failure Test.

26. The water soluble unit dose article according to claim 1, wherein the water-soluble unit dose article is a pouch and has a pouch strength of at least about 350N in accordance with the Pouch Strength Test, the water-soluble unit dose article has 0 seal failures in accordance with the Seal Failure Test, and the water-soluble unit dose article has an average Log(residue area) of less than about 6.2 per the unit dose article machine wash dissolution test method.

27. The water-soluble unit dose article according to claim 1, wherein the first water soluble film further comprises a plasticizer.

28. The water-soluble unit dose article according to claim 1, wherein the second water soluble film further comprises a plasticizer.

29. The water-soluble unit dose article of claim 27, wherein the plasticizer is selected from the group consisting of glycerine, trimethylol propane, sorbitol, and combinations thereof.

30. The water-soluble unit dose article according to claim 1, wherein the first water soluble film further comprises a surfactant.

31. The water-soluble unit dose article according to claim 1, wherein the second water soluble film further comprises a surfactant.

32. The water-soluble unit dose article of claim 30, wherein the surfactant is selected from the group consisting of polyoxyethylenated polyoxypropylene glycols, alcohol ethoxylates, alkylphenol ethoxylates, tertiary acetylenic glycols, alkanolamides, polyoxyethylenated amines, quaternary ammonium salts, quaternized polyoxyethylenated amines, amine oxides, N-alkylbetaines, sulfobetaines, and mixtures thereof.

33. The water-soluble unit dose article according to claim 1, wherein the first water soluble film further comprises an aversive agent.

34. The water-soluble unit dose article according to claim 1, wherein the second water soluble film further comprises an aversive agent.

35. The water-soluble unit dose article according to claim 1, wherein the water-soluble unit dose article comprises at least two sealed compartments, or at least three sealed compartments.

36. The water-soluble unit dose article according to claim 35, wherein the unit dose article comprises a top film, a middle film, and a bottom film, the top and bottom films comprising the first water-soluble film and the middle film comprising the second water-soluble film.

37. The water-soluble unit dose article according to claim 1, wherein the first water soluble resin comprises a polyvinyl alcohol copolymer having a degree of hydrolysis in a range of about 80% to about 99%.

38. The water-soluble unit dose article according to claim 1, wherein the second water soluble resin comprises a polyvinyl alcohol copolymer having a degree of hydrolysis in a range of about 80% to about 99%.

39. The water-soluble unit dose article according to claim 1, wherein the first water soluble resin comprises a polyvinyl alcohol homopolymer having a degree of hydrolysis in a range of about 80% to about 99%.

40. The water-soluble unit dose article according to claim 1, wherein the second water soluble resin comprises a polyvinyl alcohol homopolymer having a degree of hydrolysis in a range of about 80% to about 99%.

41. The water-soluble unit dose article according to claim 1, wherein the article contains a non-household care composition.

42. The water-soluble unit dose article according to claim 41, wherein the non-household care composition is selected from agricultural compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions.

43. The water-soluble unit dose article according to claim 42, wherein the non-household care composition comprises an agricultural composition.

44. The water-soluble unit dose article according to claim 42, wherein the non-household care composition comprises an water-treatment composition.

45. A method of making a water soluble unit dose article comprising a composition contained in the article; comprising the steps of:
contacting a first water-soluble film and a second water-soluble film along a seal area;
sealing the first water soluble film and the second water soluble film together, thereby enclosing the composition in the water soluble unit dose article;
wherein the first water-soluble film comprises a PVOH polymer comprising a first anionic content and the second water soluble film comprises a PVOH polymer comprising a second anionic content, wherein the first water-soluble film and the second water-soluble film are chemically different to one another with respect to the anionic content of the PVOH polymers of the films;
wherein the first anionic content is in a range of about 0.5 mol % to about 10 mol % of total PVOH polymer in the first water soluble film and the second anionic content is in a range of about 0 mol % to about 5 mol % of total PVOH polymer in the second water soluble film, and the difference between the first anionic content and second anionic content is about 0.05 mol % to about 4 mol %;
wherein the first water soluble film comprises a first water soluble PVOH resin and the second water soluble film comprises a second water soluble PVOH resin;
wherein the first water soluble resin comprises a first blend of at least one polyvinyl alcohol copolymer comprising an anionic monomer unit(s) and at least one polyvinyl alcohol homopolymer, the second water soluble resin comprises a second blend of at least one polyvinyl alcohol copolymer comprising an anionic monomer unit(s) and at least one polyvinyl alcohol homopolymer, and the first blend is chemically different from the second blend; and
wherein the first blend comprises a monomethyl maleate modified PVOH resin and a PVOH homopolymer resin and the second blend comprises a monomethyl maleate modified PVOH resin and a PVOH homopolymer resin;
provided that when the composition is a fabric care or household care composition and a film comprises a blend of a polyvinyl alcohol homopolymer resin and an anionic polyvinyl alcohol copolymer resin, then both then first water soluble film and the second water soluble film comprise blends that include 65 wt. % or greater of an anionic polyvinyl alcohol copolymer resin, based on the total weight of polyvinyl alcohol resins in the blend; and
provided that when the composition is a fabric care or household care composition and a film comprises a blend of at least two anionic polyvinyl alcohol copolymer resins, then both then first water soluble film and the second water soluble film comprise blends of at least two anionic polyvinyl alcohol copolymer resins.

46. Method of using a first water-soluble film and a second water-soluble film to manufacture a water-soluble unit dose article with improved seal strength and optionally comprising a composition contained in the article, wherein the first water-soluble film comprises a PVOH polymer comprising a first anionic content and the second water soluble film comprises a PVOH polymer comprising a second anionic content, wherein the first water-soluble film and the second water-soluble film are chemically different to one another with respect to the anionic content of the PVOH polymers of the films; wherein the first anionic content is in a range of about 0.5 mol % to about 10 mol % of total PVOH polymer in the first water soluble film and the second anionic content is in a range of about 0 mol % to about 5 mol % of total PVOH polymer in the second water soluble film, and the difference between the first anionic content and second anionic content is about 0.05 mol % to about 4 mol %; wherein the first water soluble film comprises a first water soluble PVOH resin and the second water soluble film comprises a second water soluble PVOH resin; wherein the first water soluble resin comprises a first blend of at least one polyvinyl alcohol copolymer comprising an anionic monomer unit(s) and at least one polyvinyl alcohol homopolymer, the second water soluble resin comprises a second blend of at least one polyvinyl alcohol copolymer comprising an anionic monomer unit(s) and at least one polyvinyl alcohol homopolymer, and the first blend is chemically different from the second blend; and wherein the first blend comprises a monomethyl maleate modified PVOH resin and a PVOH homopolymer resin and the second blend comprises a monomethyl maleate modified PVOH resin and a PVOH homopolymer resin; comprising sealing the first film and the second film together along a seal area, in order to improve the seal strength in the seal area;

provided that when the composition is a fabric care or household care composition and a film comprises a blend of a polyvinyl alcohol homopolymer resin and an anionic polyvinyl alcohol copolymer resin, then both then first water soluble film and the second water soluble film comprise blends that include 65 wt. % or greater of an anionic polyvinyl alcohol copolymer resin, based on the total weight of polyvinyl alcohol resins in the blend; and provided that when the composition is a fabric care or household care composition and a film comprises a blend of at least two anionic polyvinyl alcohol copolymer resins, then both then first water soluble film and the second water soluble film comprise blends of at least two anionic polyvinyl alcohol copolymer resins.

47. A process for dosing a unit dose article according to claim 1 comprising the steps of:
obtaining a water-soluble unit dose article according to claim 1; and
contacting the article with water to dissolve at least one of the films.

48. The water-soluble unit dose article of claim 1 comprising at least one sealed compartment comprising at least one composition contained in the article,
wherein the first anionic content ranges from about 1 mol % to about 4 mol % of total PVOH polymer in the first water soluble film and the second anionic content ranges from about 0.1 mol % to about 3 mol % of total PVOH polymer in the second water soluble film, and the difference between the first anionic content and second anionic content is about 0.05 mol %.

49. The water-soluble unit dose article of claim 48, wherein the first blend of PVOH polymer resins comprises from about 10 wt % to about 70 wt % by weight of monomethyl maleate modified PVOH resin.

50. The water-soluble unit dose article of claim 48, wherein the second blend of PVOH polymer resins comprises from about 10 wt % to about 70 wt % by weight of monomethyl maleate modified PVOH resin.

51. The water-soluble unit dose article of claim 48, wherein the first blend of PVOH polymer resins comprises from about 10 wt % to about 32 wt % by weight of monomethyl maleate modified PVOH resin and the second blend of PVOH polymer resins comprises from about 33 wt % to about 50 wt % by weight of monomethyl maleate modified PVOH resin.

52. The water-soluble unit dose article according to claim 48, wherein the first water soluble film is a thermoformed film.

53. The water-soluble unit dose article according to claim 48, wherein the second water soluble film is not a thermoformed film.

54. The water-soluble unit dose article according to claim 48, wherein the anionic content of the a first water soluble film or the a second water soluble film further comprises an anionic monomer unit derived from a monomer selected from the group consisting of vinyl acetic acid, alkyl acrylates, maleic acid, monoalkyl maleate other than monomethyl maleate, dialkyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts thereof, esters thereof, and combinations thereof.

55. The water-soluble unit dose article of claim 54, wherein the further anionic monomer unit is derived from a monomer selected from the group consisting of maleic acid, monoalkyl maleate other than monomethyl maleate, dialkyl maleate, maleic anhydride, alkali metal salts thereof, esters thereof, and combinations thereof.

56. The water-soluble unit dose article according to claim 48, wherein the monomethyl maleate modified PVOH resin has a degree of hydrolysis in a range of about 80% to about 99%.

57. The water-soluble unit dose article according to claim 48, wherein the PVOH homopolymer resin has a degree of hydrolysis in a range of about 80% to about 99%.

* * * * *

UNITED STATES PATENT AND TRADEMARK OFFICE
CERTIFICATE OF CORRECTION

PATENT NO. : 11,473,039 B2  
APPLICATION NO. : 16/601224  
DATED : October 18, 2022  
INVENTOR(S) : Philip Frank Souter et al.

Page 1 of 1

It is certified that error appears in the above-identified patent and that said Letters Patent is hereby corrected as shown below:

In the Claims

Column 27, Line 53, In Claim 1, "comprising" should be -- comprising: --.

Column 27, Line 53, In Claim 1, "a first water soluble film comprising a" should be at Line 54, before "PVOH", as a new sub-point.

Column 28, Line 46, In Claim 1, "both then" should be -- both the --.

Column 29, Line 59, In Claim 15, "the a" should be -- the --.

Column 29, Line 60, In Claim 15, "the a" should be -- the --.

Column 32, Lines 47-48, In Claim 45, "both then" should be -- both the --.

Column 32, Line 56, In Claim 45, "both then" should be -- both the --.

Column 33, Lines 29-30, In Claim 46, "both then" should be -- both the --.

Column 33, Line 38, In Claim 46, "both then" should be -- both the --.

Column 33, Line 56, In Claim 48, "0.05 mol %." should be -- 0.05 mol % to about 2 mol %. --.

Column 34, Line 23, In Claim 53, "the a" should be -- the --.

Column 34, Line 24, In Claim 54, "the a" should be -- the --.

Signed and Sealed this  
Twentieth Day of June, 2023

Katherine Kelly Vidal  
*Director of the United States Patent and Trademark Office*